US011986327B2

(12) United States Patent
Gregerson et al.

(10) Patent No.: US 11,986,327 B2
(45) Date of Patent: May 21, 2024

(54) MEDICAL X-RAY IMAGING SYSTEMS AND METHODS

(71) Applicant: Mobius Imaging, LLC, Shirley, MA (US)

(72) Inventors: Eugene A. Gregerson, Bolton, MA (US); Russell Stanton, Lunenberg, MA (US)

(73) Assignee: Mobius Imaging, LLC, Shirley, MA (US)

( * ) Notice: Subject to any disclaimer, the term of this patent is extended or adjusted under 35 U.S.C. 154(b) by 372 days.

(21) Appl. No.: 17/524,201

(22) Filed: Nov. 11, 2021

(65) Prior Publication Data

US 2022/0061780 A1 Mar. 3, 2022

Related U.S. Application Data

(63) Continuation of application No. 16/354,047, filed on Mar. 14, 2019, now Pat. No. 11,197,643.

(Continued)

(51) Int. Cl.
*A61B 6/03* (2006.01)
*A61B 6/00* (2006.01)
(Continued)

(52) U.S. Cl.
CPC ............ *A61B 6/035* (2013.01); *A61B 6/4405* (2013.01); *A61B 6/4411* (2013.01);
(Continued)

(58) Field of Classification Search
CPC ..... A61B 6/035; A61B 6/4405; A61B 6/4411; A61B 6/4429; A61B 6/4447; A61B 6/54;
(Continued)

(56) References Cited

U.S. PATENT DOCUMENTS 4,442,489 A 4/1984 Wagner
4,709,382 A 11/1987 Sones
(Continued)

FOREIGN PATENT DOCUMENTS

WO 2016077138 A1 5/2016

OTHER PUBLICATIONS

International Search Report for Application No. PCT/US 2019/022509 dated Aug. 21, 2019, 5 pages.

*Primary Examiner* — David P Porta
*Assistant Examiner* — Fani Polyzos Boosalis
(74) *Attorney, Agent, or Firm* — Howard & Howard Attorneys PLLC

(57) ABSTRACT

A detector system for an x-ray imaging device includes a detector chassis, a plurality of sub-assemblies mounted to the detector chassis and within an interior housing of the chassis, the sub-assemblies defining a detector surface, where each sub-assembly includes a thermally-conductive support mounted to the detector chassis, a detector module having an array of x-ray sensitive detector elements mounted to a first surface of the support, an electronics board mounted to a second surface of the support opposite the first surface, at least one electrical connector that connects the detector module to the electronics board, where the electronics board provides power to the detector module and receives digital x-ray image data from the detector module via the at least one electrical connector. Further embodiments include x-ray imaging systems, external beam radiation treatment systems having an integrated x-ray imaging system, and methods therefor.

22 Claims, 23 Drawing Sheets

Related U.S. Application Data

(60) Provisional application No. 62/644,032, filed on Mar. 16, 2018.

(51) Int. Cl.
   *A61N 5/10*      (2006.01)
   *H01L 27/146*    (2006.01)
   *A61B 6/42*      (2024.01)
   *A61B 6/58*      (2024.01)

(52) U.S. Cl.
   CPC .......... *A61B 6/4429* (2013.01); *A61B 6/4447* (2013.01); *A61B 6/54* (2013.01); *A61N 5/1064* (2013.01); *H01L 27/14618* (2013.01); *A61B 6/4266* (2013.01); *A61B 6/4291* (2013.01); *A61B 6/587* (2013.01); *A61B 6/588* (2013.01); *A61B 2560/0437* (2013.01); *A61B 2560/0443* (2013.01); *A61B 2562/166* (2013.01); *A61B 2562/227* (2013.01); *G01N 2223/301* (2013.01); *G01N 2223/321* (2013.01); *G01N 2223/3303* (2013.01); *G01N 2223/3304* (2013.01)

(58) Field of Classification Search
   CPC ..... A61B 6/4266; A61B 6/4291; A61B 6/587; A61B 6/588; A61B 2560/0437; A61B 2560/0443; A61B 2562/166; A61B 2562/227; A61N 5/1064; H01L 27/14618; G01N 2223/301; G01N 2223/321; G01N 2223/3303; G01N 2223/3304
   See application file for complete search history.

(56) References Cited

U.S. PATENT DOCUMENTS

| | | |
|---|---|---|
| 4,928,283 A | 5/1990 | Gordon |
| 5,448,607 A | 9/1995 | McKenna |
| 5,592,523 A | 1/1997 | Tuy et al. |
| 5,740,222 A | 4/1998 | Fujita et al. |
| 6,041,097 A | 3/2000 | Roos et al. |
| 6,075,836 A | 6/2000 | Ning |
| 6,104,775 A | 8/2000 | Tuy |
| 6,212,251 B1 | 4/2001 | Tomura et al. |
| 6,243,438 B1 | 6/2001 | Nahaliel et al. |
| 6,304,625 B1 | 10/2001 | Senzig |
| 6,426,989 B2 | 7/2002 | Grass et al. |
| 6,490,333 B1 | 12/2002 | Hsieh |
| 6,700,948 B2 | 3/2004 | Hoffman |
| 6,744,844 B2 | 6/2004 | Horiuchi |
| 6,988,827 B2 | 1/2006 | Mueller |
| 6,996,204 B2 | 2/2006 | Grass et al. |
| 7,001,045 B2 | 2/2006 | Gregerson et al. |
| 7,175,347 B2 | 2/2007 | Tybinkowski et al. |
| 7,215,805 B2 | 5/2007 | Bruder et al. |
| 7,224,764 B2 | 5/2007 | Sukovic et al. |
| 7,388,941 B2 | 6/2008 | Sukovic et al. |
| 7,394,888 B2 | 7/2008 | Sukovic et al. |
| 7,397,895 B2 | 7/2008 | Bailey et al. |
| 7,489,516 B2 | 2/2009 | Lacey |
| 7,532,702 B2 | 5/2009 | Hsieh et al. |
| 7,568,836 B2 | 8/2009 | Bailey et al. |
| 7,637,660 B2 | 12/2009 | Tybinkowski et al. |
| 7,963,696 B2 | 6/2011 | Bailey et al. |
| 8,031,828 B1 | 10/2011 | DeMan et al. |
| 8,251,584 B2 | 8/2012 | Tybinkowski et al. |
| 8,705,695 B2 | 4/2014 | Jabri et al. |
| 8,737,708 B2 | 5/2014 | Hartmann et al. |
| 8,746,973 B2 | 6/2014 | Gregerson et al. |
| 8,753,009 B2 | 6/2014 | Gregerson et al. |
| 8,888,364 B2 | 11/2014 | Bailey et al. |
| 8,890,079 B2 | 11/2014 | Kurochi et al. |
| 8,987,675 B2 | 3/2015 | Kato |
| 9,016,941 B2 | 4/2015 | Tybinkowski et al. |
| 9,111,379 B2 | 8/2015 | Gregerson et al. |
| 9,125,613 B2 | 9/2015 | Gregerson et al. |
| 9,398,886 B2 | 7/2016 | Gregerson et al. |
| 9,788,804 B2 | 10/2017 | Bailey et al. |
| 9,795,022 B2 | 10/2017 | Duhamel |
| 9,820,704 B2 | 11/2017 | Tybinkowski et al. |
| 9,968,314 B1 | 5/2018 | Sebring |
| 10,178,981 B2 | 1/2019 | Bailey et al. |
| 10,307,117 B2 | 6/2019 | Park et al. |
| 2002/0054659 A1 | 5/2002 | Okumura et al. |
| 2005/0135560 A1 | 6/2005 | Dafni et al. |
| 2007/0104317 A1 | 5/2007 | Ohishi |
| 2007/0280410 A1 | 12/2007 | Lutz et al. |
| 2009/0252285 A1 | 10/2009 | Shapiro et al. |
| 2010/0215142 A1 | 8/2010 | Dafni et al. |
| 2011/0116595 A1 | 5/2011 | Carmi et al. |
| 2012/0069956 A1 | 3/2012 | Guery et al. |
| 2013/0034200 A1 | 2/2013 | Hsieh et al. |
| 2013/0051519 A1 | 2/2013 | Yang et al. |
| 2013/0343507 A1 | 12/2013 | Gregerson et al. |
| 2014/0265182 A1 | 9/2014 | Stanton et al. |
| 2015/0119704 A1* | 4/2015 | Roth ............... A61B 6/547 600/425 |
| 2015/0374322 A1 | 12/2015 | Gregerson et al. |
| 2016/0046860 A1 | 2/2016 | Wang et al. |
| 2017/0007334 A1 | 1/2017 | Crawford et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0322619 A1 | 11/2017 | Eismann et al. |
| 2018/0055707 A1 | 3/2018 | Stanton |
| 2018/0177473 A1 | 6/2018 | Gregerson et al. |
| 2018/0214098 A1 | 8/2018 | Tybinkowski et al. |
| 2019/0282185 A1* | 9/2019 | Gregerson ........... A61B 6/4488 |

\* cited by examiner

MEDICAL X-RAY IMAGING SYSTEMS AND METHODS

RELATED APPLICATIONS

This application is a Continuation of U.S. patent application Ser. No. 16/354,047, filed on Mar. 14, 2019, which claims priority to and the benefit of U.S. Provisional Patent Application No. 62/644,032, filed Mar. 16, 2018, the disclosures of each of which are hereby incorporated by reference in their entirety.

BACKGROUND

Conventional medical imaging devices, such as x-ray computed tomography (CT) imaging devices, are limited in the types of imaging operations that may be performed.

SUMMARY

Embodiments include detector systems for an x-ray imaging device, x-ray imaging systems, external beam radiation treatment systems having an integrated x-ray imaging system, and methods therefor.

An embodiment includes a detector system for an x-ray imaging device that includes a detector chassis defining an interior housing, and a plurality of sub-assemblies mounted to the detector chassis within the interior housing, the plurality of sub-assemblies defining a detector surface, where each sub-assembly of the plurality of sub-assemblies includes a thermally-conductive support mounted to the detector chassis, a detector module including an array of x-ray sensitive detector elements mounted to a first surface of the support, an electronics board mounted to a second surface of the support that is opposite the first surface of the support, at least one electrical connector that connects the detector module to the electronics board, where the electronics board provides power to the detector module and receives digital x-ray image data from the detector module via the at least one electrical connector.

Further embodiments include an x-ray imaging system that includes an O-shaped gantry comprising a housing and defining an imaging bore, an x-ray source located within the housing of the gantry, a detector system located within the housing of the gantry opposite the x-ray source, the detector system including a plurality of x-ray sensitive detector elements defining a contiguous detector area, the detector area having an elongated central portion having a length of at least about 1 meter and a pair of peripheral portions extending on either side of the central portion to define a panel region having a width of greater than 0.3 meters and a length that is less than 0.5 meters, and a drive system for rotating the x-ray source and the detector system around the imaging bore.

Further embodiments include an x-ray imaging system that includes an O-shaped gantry comprising a housing and defining an imaging bore, an x-ray source located within the housing of the gantry, a detector located within the housing of the gantry opposite the x-ray source, the detector including a two-dimensional array of pixels, the array having a length and a width dimension of greater than about 0.3 meters, an apparatus for moving the detector array relative to the x-ray source by a distance that is less than a spacing between adjacent pixels of the detector array, a drive system for rotating the x-ray source and the detector system around an object located in the imaging bore, a processing device, coupled to the detector, that is configured with processor-executable instructions to perform operations including receiving, from the detector, a plurality of first x-ray images of the object with a first spatial resolution that are obtained while the detector array is moved relative to the x-ray source, and generating at least one second image of the object using the plurality of first x-ray images, wherein the at least one second image is a super resolution (SR) image that has an improved spatial resolution and/or signal-to-noise (SNR) ratio compared to the first images.

Further embodiments include an x-ray imaging system that includes an O-shaped gantry comprising a housing and defining an imaging bore, a drive mechanism for moving the gantry with respect to a patient located within the imaging bore of the gantry, an x-ray source located within the housing of the gantry, a detector located within the housing of the gantry opposite the x-ray source, the detector including a two-dimensional array of pixels, the array having a length and a width dimension of greater than about 0.3 meters, a rotation drive system configured to rotate the x-ray source and the detector around the patient located in the imaging bore, and a control system, coupled to the drive mechanism, and including a processor that is configured with processor-executable instructions to perform operations including controlling the drive mechanism to move the x-ray source and detector system relative to the patient located within the bore of the gantry as the x-ray source and detector system rotate around the patient so that the x-ray source and detector system follow a sinusoidal scan trajectory around the patient.

Further embodiments include an x-ray imaging system that includes an O-shaped gantry including a housing and defining an imaging bore, a drive mechanism configured to translate the gantry with respect to a patient located within the imaging bore, an x-ray source located within the housing of the gantry, a detector located within the housing of the gantry opposite the x-ray source, the detector including a two-dimensional array of pixels, the array having a length and a width dimension of greater than about 0.3 meters, a rotation drive system configured to rotate the x-ray source and the detector around the patient located in the imaging bore, and a control system, coupled to the drive mechanism and to the rotation drive system, and including a processor that is configured with processor-executable instructions to perform operations including controlling the rotation drive system to rotate the x-ray source and the detector around a patient located in the bore of the gantry in a first rotational direction and then in a second rotational direction that is opposite the first direction; and controlling the drive mechanism to translate the gantry in a first translation direction along the length of the patient as the x-ray source and detector system rotate around the patient in the first rotational direction and in the second rotational direction so that the x-ray source and detector follow a reverse helical scan trajectory around the patient.

Further embodiments include an external beam radiation treatment system that includes a rotatable gantry having a head that emits a radiation treatment beam, the rotatable gantry configured to rotate around a patient to direct the radiation treatment beam to a target location within the patient from different angles, an x-ray imaging system mounted to the rotatable gantry, the x-ray imaging system including an x-ray source, a detector opposite the x-ray source, a first actuator system for moving the x-ray source relative to the rotatable gantry, and a second actuator system for moving the detector relative to the rotatable gantry, and a control system, coupled to the first actuator system and to the second actuator system, and including a processor that is configured with processor-executable instructions to perform operations including controlling the first actuator system and the second actuator system to move the x-ray source and the detector relative to a patient as the gantry rotates around the patient so that the x-ray source and the detector follow a sinusoidal scan trajectory around the patient.

Further embodiments include an external beam radiation treatment system that includes a rotatable gantry having a head that emits a radiation treatment beam, the rotatable gantry configured to rotate around a patient to direct the radiation treatment beam to a target location within the patient from different angles, an x-ray imaging system mounted to the rotatable gantry, the x-ray imaging system including an x-ray source, a detector opposite the x-ray source, the detector including a two-dimensional array of pixels having a pixel spacing between adjacent pixels, and an apparatus for moving the detector array relative to the x-ray source by a distance that is less than the pixel spacing, and a processing device, coupled to the detector, that is configured with processor-executable instructions to perform operations including receiving, from the detector, a plurality of first x-ray images of the patient with a first spatial resolution that are obtained while the detector array is moved relative to the x-ray source by a distance that is less than the pixel spacing, and generating at least one second image of the object using the plurality of first x-ray images, wherein the at least one second image is a super resolution (SR) image that has an improved spatial resolution and/or signal-to-noise (SNR) ratio compared to the first images.

Further embodiments include an external beam radiation treatment system that includes a rotatable gantry having a head that emits a radiation treatment beam, the rotatable gantry configured to rotate around a patient to direct the radiation treatment beam to a target location within the patient from different angles, an x-ray imaging system mounted to the rotatable gantry, the x-ray imaging system including an x-ray source, a detector opposite the x-ray source, a first actuator system for moving the x-ray source relative to the rotatable gantry, and a second actuator system for moving the detector relative to the rotatable gantry, and a control system, coupled to the gantry, the first actuator system and the second actuator system, and including a processor that is configured with processor-executable instructions to perform operations including controlling the gantry to rotate the x-ray source and the x-ray detector around the patient in a first rotational direction and then in a second rotational direction that is opposite the first direction, controlling the first actuator system and the second actuator system to translate the x-ray source and detector system in a first translation direction along the length of the patient as the x-ray source and detector system rotate around the patient in the first rotational direction and the second rotational direction so that the x-ray source and detector system follow a reverse helical scan trajectory around the patient.

BRIEF DESCRIPTION OF THE DRAWINGS

Other features and advantages of the present invention will be apparent from the following detailed description of the invention, taken in conjunction with the accompanying drawings of which.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Figure 1:
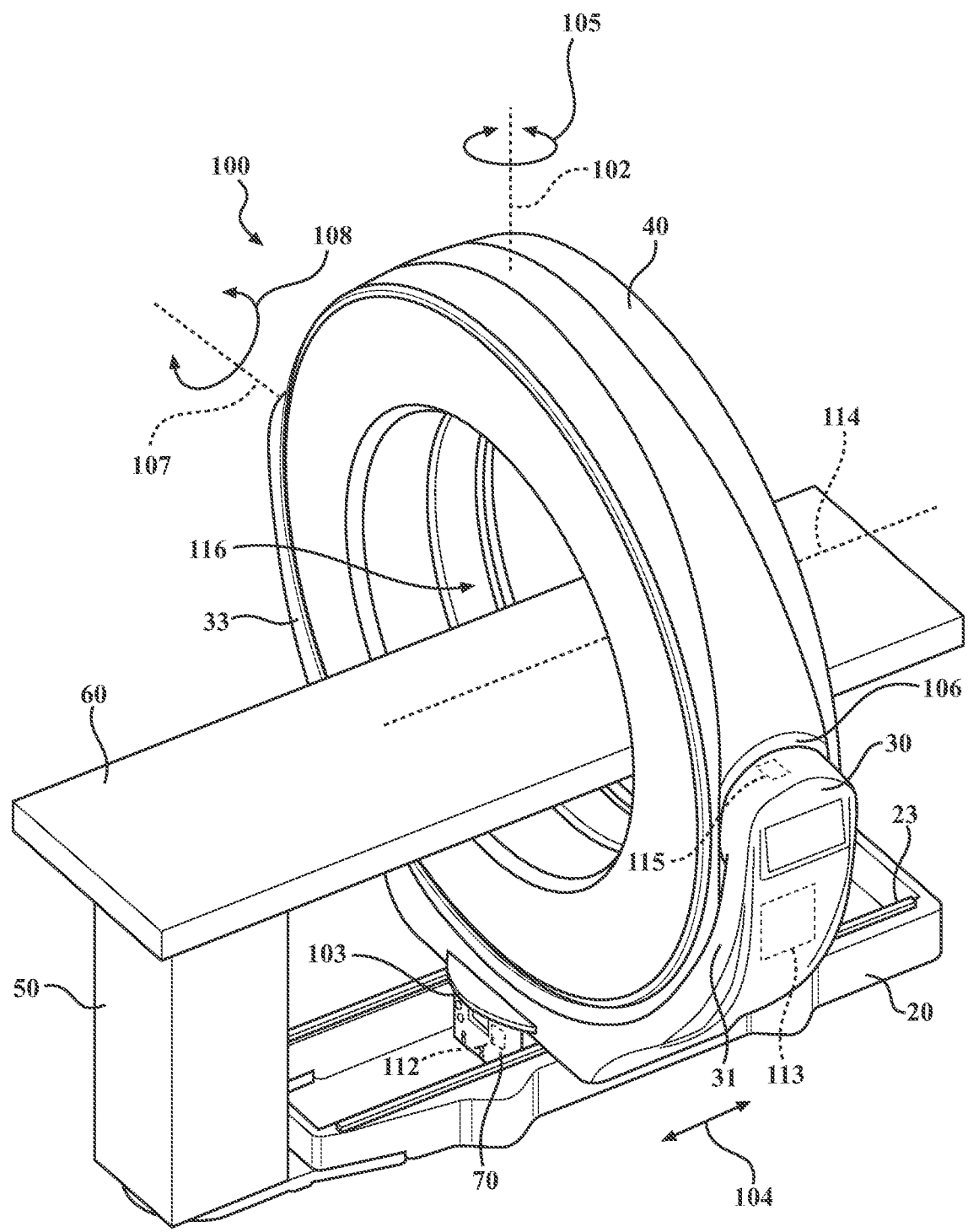
FIG. 1 illustrates a mobile x-ray imaging system.

An imaging system 100 according to one embodiment is shown in FIG. 1. The imaging system 100 may be a mobile imaging system 100, and may include a base 20, a gimbal 30 and a gantry 40. The system 100 includes image collection and generation components, such as an x-ray source and an x-ray detector system that are housed within the gantry 40. The gantry 40 may be a generally O-shaped structure having a central imaging bore 116 and defining an imaging axis 114 extending through the bore. The system 100 is configured to collect imaging data, such as 3D x-ray tomographic image data and/or 2D x-ray fluoroscopic images, for example, from an object (e.g., human or animal patient) located within the bore 116 of the gantry 40. In the embodiment of FIG. 1, a column 50 is attached to the base 20 and supports a table 60 (e.g., a patient table) in a cantilevered manner such that the table 60 extends over the base 20 and at least partially into the bore 116 of the gantry 40. It will be understood that in other embodiments, the column 50 and table 60 may not be attached to the base 20.

The gimbal 30 may be a generally U-shaped support that is mounted to the top surface of base 20 and includes a pair of arms 31, 33 extending up from the base. The arms 31, 33 may be connected to opposite sides of gantry 40 so that the gantry is suspended above the base 20 and gimbal 30. A drive system 70 may drive the translation (z-axis translation) of the gimbal 30 and the gantry 40 relative to the base 20 in the direction of arrow 104 shown in FIG. 1. The drive system 70 may be mounted beneath the gimbal 30 within an open region of the base 20, as shown in FIG. 1. A control system 113 (e.g., a processor and memory) may be operatively coupled to the drive system 70 and may control the translation of the gimbal 30 and gantry 40 along the base 20 when the imaging system 100 is in a scan position (i.e., lowered to the floor). The control system 113 may be located on the imaging system 100, such as on the gimbal 30. A pair of rails 23 located on the top surface of the base 20 may engage with bearing elements on the bottom of the gimbal 30 to guide the translation of the gimbal 30 and gantry 40 along the base 20.

The system 100 of FIG. 1 is a mobile system in which the entire system (including the base 20, gimbal 30 and gantry 40) may be moved across the floor (e.g., via one or more wheels or casters) for transport and/or repositioning of the system. For example, the base 20 may be raised from the floor while a plurality of casters are extended from the bottom of the base 20 and the entire system 100 may be driven in a transport mode. To perform an imaging procedure, the base 20 may be lowered to the ground and the gimbal 30 and gantry 40 may be translated along the length of the base 20 (e.g., to perform a CT scan). In the embodiment of FIG. 1, the drive mechanism for transporting the entire system and the drive mechanism for translating the gimbal 30 and gantry 40 may be separate drive systems mounted beneath the gimbal 30, which are collectively illustrated as drive system 70 in FIG. 1. Various embodiments of a drive system 70 for a mobile imaging system as shown in FIG. 1 are described in U.S. Pat. No. 8,753,009 and U.S. Published Patent Application No. 2014/0265182, which are incorporated by reference herein.

The gantry 40 and at least an upper portion of the gimbal 30 may rotate on a rotary bearing 103 with respect to the base 20. The rotation of the gantry 40 and gimbal 30 may be about a vertically-extending axis 102 in the direction of arrow 105 in FIG. 1. The axis 102 may extend through the isocenter of the imaging gantry 40. In some embodiments, a motorized system 112 as shown schematically in FIG. 1 may drive the rotation of the gantry 40 and gimbal 30 about axis 102. The motorized system 112 may be operatively coupled to and controlled by a system controller 113.

The gantry 40 may rotate (i.e., tilt) with respect to the gimbal 30 on a pair of rotary bearings 106 that attach the gantry 40 to the arms 31, 33 of the gimbal 30. The tilting motion of the gantry 40 may be about a horizontally-extending axis 107 in the direction of arrow 108 in FIG. 1. The axis 107 may extend through the isocenter of the imaging gantry 40. In some embodiments, a motorized system 115 shown schematically in FIG. 1 may drive the tilt motion of the gantry 40 relative to the gimbal 30. The motorized system 115 may be operatively coupled to and controlled by a system controller 113.

Figure 2:
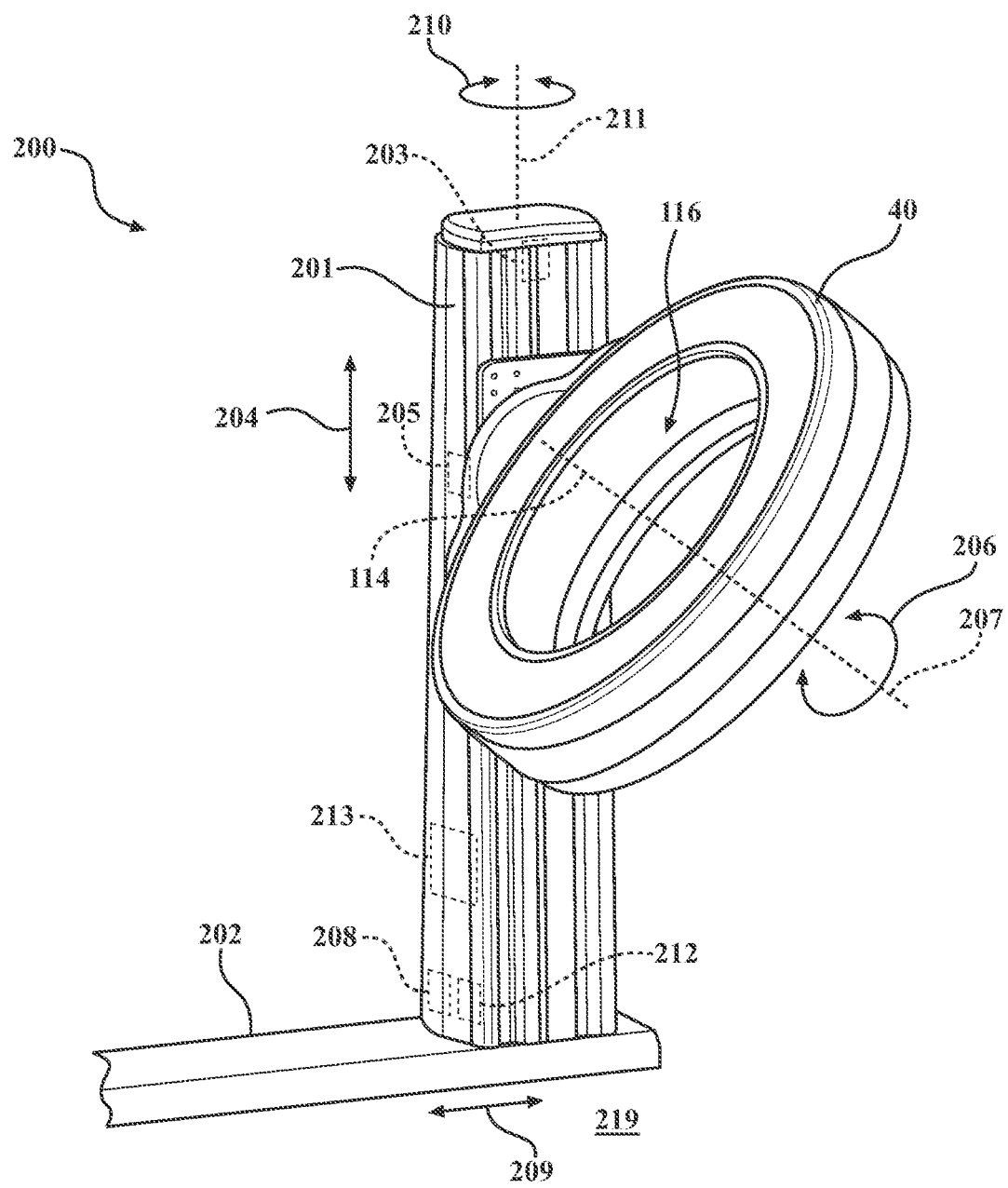
FIG. 2 illustrates a multi-axis x-ray imaging system having a cantilevered imaging gantry.

FIG. 2 illustrates another imaging system 200 according to an embodiment. The system 200 includes a gantry 40 that houses image collection components, such as a rotating x-ray source and detector array, that may be similar to the gantry 40 in the system 100 of FIG. 1. The gantry 40 in system 200 may be mounted to a support column 201. The support column 201 may be attached to the gantry 40 on a first side of the gantry 40 and may support the gantry 40 in a cantilevered manner. The gantry 40 may be a generally O-shaped structure having a central imaging bore 116 and defining an imaging axis 114 extending through the bore.

The system 200 may also include a base 202 that may be located on a weight-bearing surface, such as a floor 219 of a building. In the illustrated embodiment, the base 202 comprises a generally rectilinear support structure that may be mounted (e.g., bolted) to the floor 219. The support column 201 may be located on and supported by the base 202 and may extend upwards from the top surface of the base 202 in a generally vertical direction. The support column 201 may have a length dimension that extends vertically at least about 2 meters, such as 2-5 meters (e.g., about 3 meters).

In various embodiments, the system 200 may enable imaging (e.g., CT scanning, x-ray fluoroscopy) in multiple orientations and along multiple directions. In embodiments, the system 200 may include a first drive mechanism 203 for translating the gantry 40 relative to the support column 201 in a first direction along the direction of arrow 204 in FIG. 2. The first direction 204 may be a generally vertical direction (i.e., perpendicular to the floor 219), which for the purposes of this disclosure may be defined as ±15° from true vertical. The system 200 may also include a second drive mechanism 205 for rotating the gantry 40 relative to the support column 201 in the direction indicated by arrow 206. The rotation of the gantry 40 may be with respect to an axis 207 that extends orthogonal to the first direction 204 and may be generally parallel to the floor 219. The axis 207 may extend through the isocenter of the bore 116 of the gantry 40. The system may also include a third drive mechanism 208 for translating the gantry 40 and support column 201 with respect to the base 202 in a second direction indicated by arrow 209 in FIG. 2. The second direction 209 may be a generally horizontal direction (i.e., parallel to the floor 219), which for the purposes of this disclosure may be defined as ±15° from true horizontal. The second direction 209 may be orthogonal to both the first direction 204 and to the rotation axis 207.

In some embodiments, the gantry 40 may also pivot relative to the base 202. For example, at least a portion of the support column 201 to which the gantry 40 is attached may rotate with respect to the base 202 in the direction of arrow 210 in FIG. 2. A fourth drive mechanism 212 may drive the rotation of the support column 201. The rotation of the support column 201 may cause the gantry 40 to pivot on the base 202. The pivoting of the gantry 40 may be about a pivot axis 211 as shown in FIG. 2.

The first drive mechanism 203, the second drive mechanism 205, the third drive mechanism 208 and/or the fourth drive mechanism 212 may be operatively coupled to and controlled by a system controller 213 that may be similar to the system controller 113 of FIG. 1.

The imaging system 200 of FIG. 2 may enable imaging, including CT scanning and x-ray fluoroscopic imaging, of a human or animal patient in a horizontal orientation (e.g., lying on a patient table 60 as shown in FIG. 1), in a vertical orientation (i.e., in a standing, weight-bearing position), or in a tilted orientation between a horizontal and vertical orientation. For example, the system 200 may perform a horizontal imaging scan (e.g., a helical CT scan) by translating the gantry 40 and support column 201 along the length of the base 202 with the imaging axis 114 extending horizontally along the length of a patient lying on a table (not shown for clarity). The system 200 may perform a vertical imaging scan by translating the gantry 40 along the length of the support column 201 with the imaging axis 114 extending vertically along the length of a patient supported in a weight-bearing position on a support structure (not shown) or standing directly on the floor 219. The system 200 may also perform an imaging scan along an angled or oblique (i.e., neither vertical or horizontal) direction. Such a scan may be performed by rotating the gantry 40 on the support column 201 so that the imaging axis extends along the desired angle while performing coordinated translations of the gantry 40 along the length of the support column 201 and the support column 201 and gantry 40 along the length of the base 202. Embodiments of a cantilevered multi-axis imaging system 200 such as shown in FIG. 2 are described in U.S. patent application Ser. No. 15/817,672, filed on Nov. 20, 2017, the contents of which are incorporated by reference herein. Embodiments of a patient table that may be used with a cantilevered multi-axis imaging system 200 for performing vertical, horizontal and/or angled imaging scans are described in U.S. Patent Application Publication No. 2018/0055707, the contents of which are incorporated by reference herein.

Figure 3:
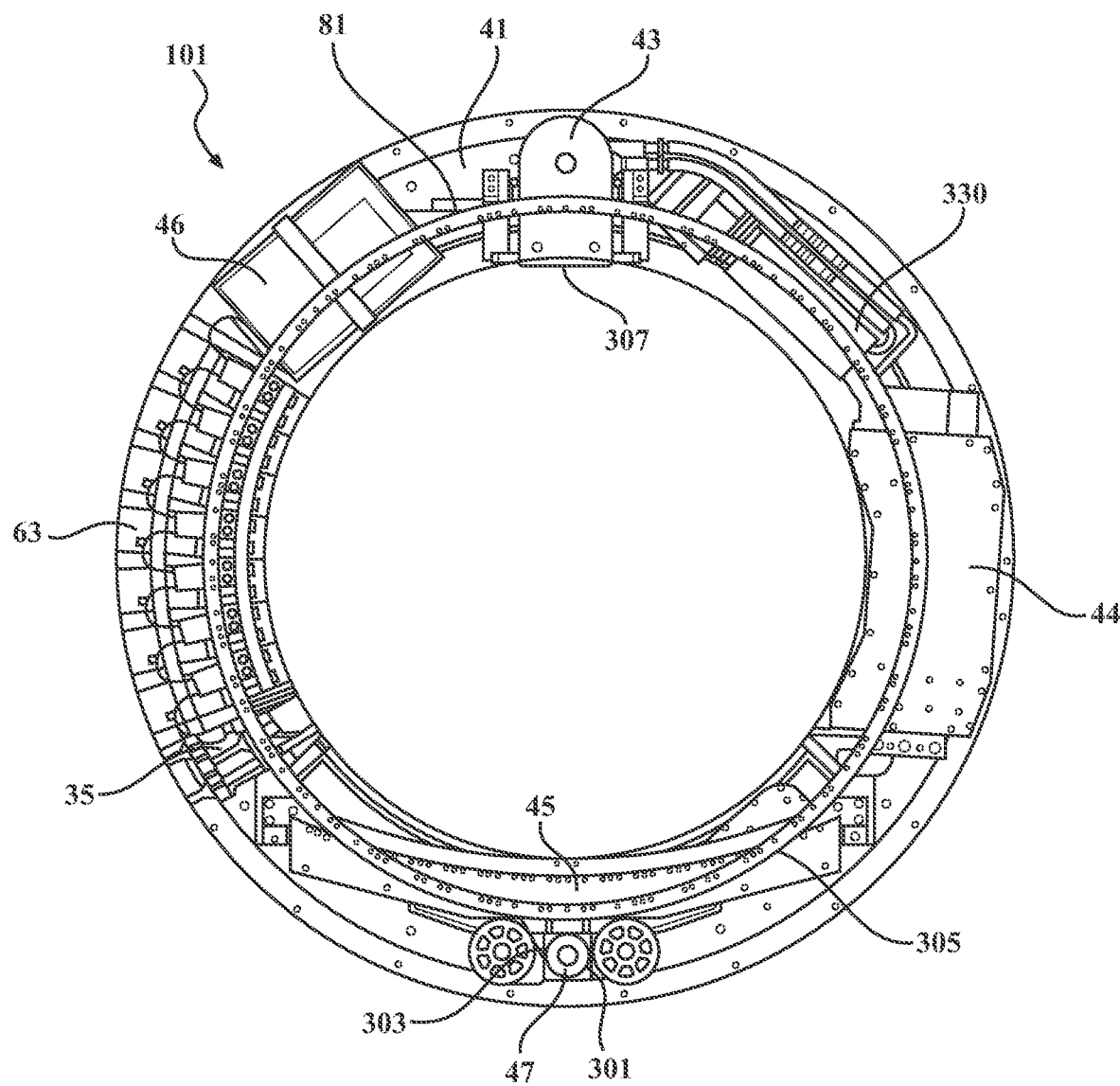
FIG. 3 illustrates components mounted to a rotor of an x-ray imaging system.

The gantry 40 in systems 100 and 200 may include an outer shell comprised of a high-strength structural material, such as aluminum. A rotor may be attached to the gantry shell via a bearing assembly that enables the rotor to rotate within the gantry 40. FIG. 3 illustrates a rotor 41 for an x-ray CT imaging system having a plurality of components mounted thereto. The rotor 41 shown in FIG. 3 includes an x-ray source 43, a high-voltage generator 44, a heat exchanger 330, an x-ray detector 45, a power supply 63 (e.g., battery system), a computer 46, a rotor drive mechanism 47, and a docking system 35 (e.g., for providing intermittent power/data connection between components mounted to the rotor 41 and non-rotating portions of the system). It will be understood that the components described and illustrated are merely exemplary, and other embodiments may omit one or more of these components and may utilize other additional components. For example, in embodiments, power for the components on the rotor 41 may be provided by a slip ring or cable system, so that a power supply 63 on the rotor may not be needed. In some embodiments, power and/or data may be continuously transferred between rotating and non-rotating portions of the system via a cable, slip ring and/or wirelessly, in which case the power supply 63, computer 46 and/or docking system 35 may not be included. Further, the rotation of the rotor 41 may be provided by a drive system on the non-rotating portion, in which case the rotor drive mechanism 47 on the rotor 41 may not be included.

In embodiments, the x-ray source 43 and detector 45 may be configured to perform a helical x-ray CT scan. The detector 45 may comprise a plurality of x-ray sensitive detector elements arranged in a generally semicircular arc, with the arc center coinciding with the focal spot of the x-ray source. Alternately, the x-ray detector may be a flat panel detector, and the system may be configured to perform real time x-ray fluoroscopic and/or cone beam imaging of an object within the bore of the gantry.

In the embodiment of FIG. 3, during an imaging scan, the rotor 41 rotates within the interior of the gantry 40, while the imaging components such as the x-ray source 43 and x-ray detector 45 obtain imaging data for an object positioned within the bore 116 of the gantry. The rotor drive mechanism 47 may drive the rotation of the rotor 41 around the interior of the gantry 40. In embodiments, the rotor drive mechanism 47 may include a drive wheel 301 that engages with a belt 303. The belt 303 may extend around the gantry 40 on a circular rail 305 that may be fixed to an interior wall of the gantry shell. The rotor drive mechanism 47 may be controlled by a system controller that controls the rotation and precise angular position of the rotor 41 with respect to the gantry 40, preferably using position feedback data, such as from an encoder device. The rotation of the rotor 41 around the imaging bore 116 may be coordinated with a motion of the gantry 40 relative to the patient (e.g., a translation of the gantry 40 along the length of the patient using a system 100, 200 as described above) to perform an imaging scan of a region of interest of the patient. Image data from the detector system 45 may be provided to a processing system (e.g., computer 46) for generating a tomographic reconstruction of the region of interest.

Figure 4A:
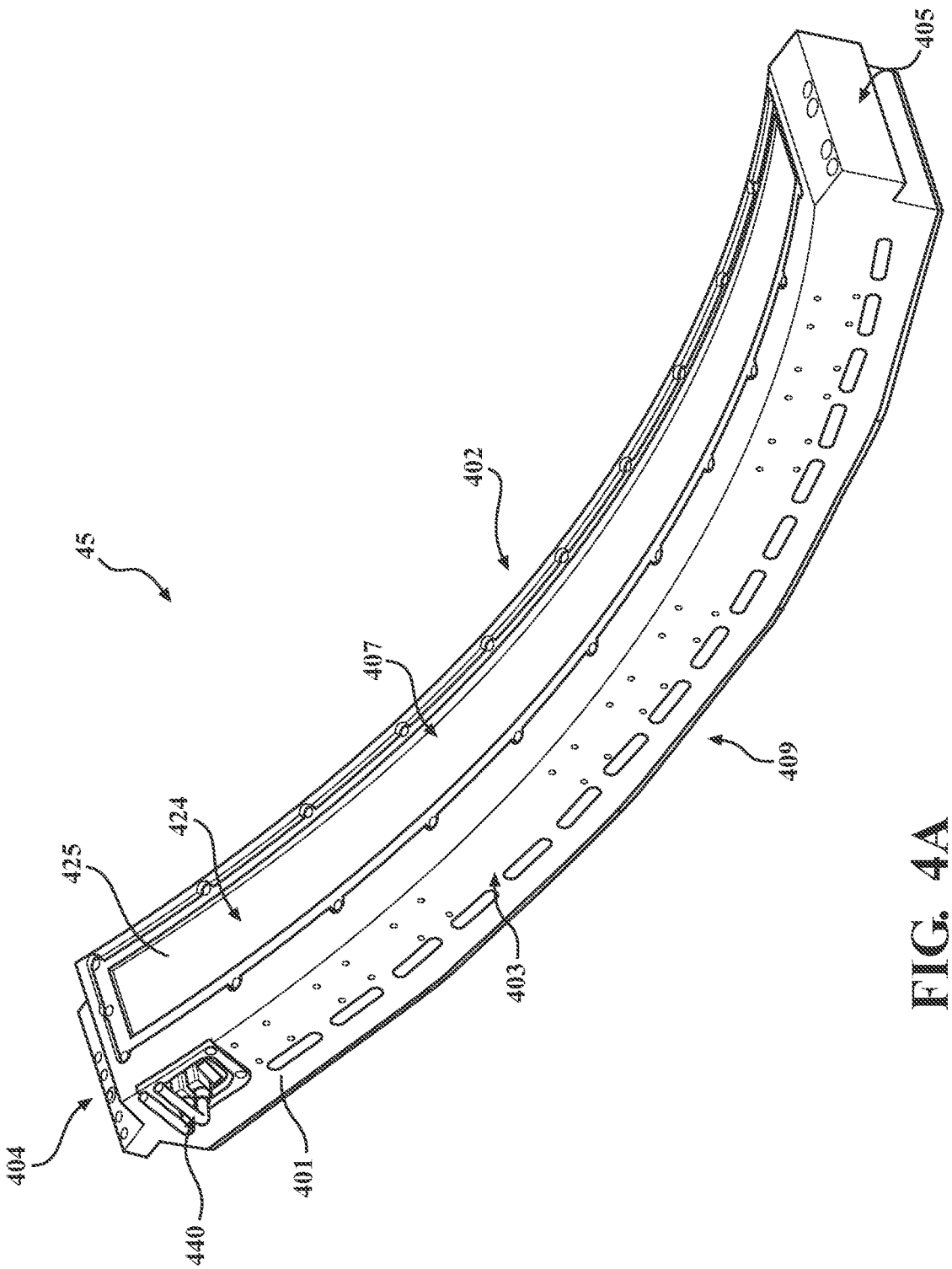
FIGS. 4A-4G illustrate a detector system for an x-ray imaging system according to various embodiments.
Figure 4B:
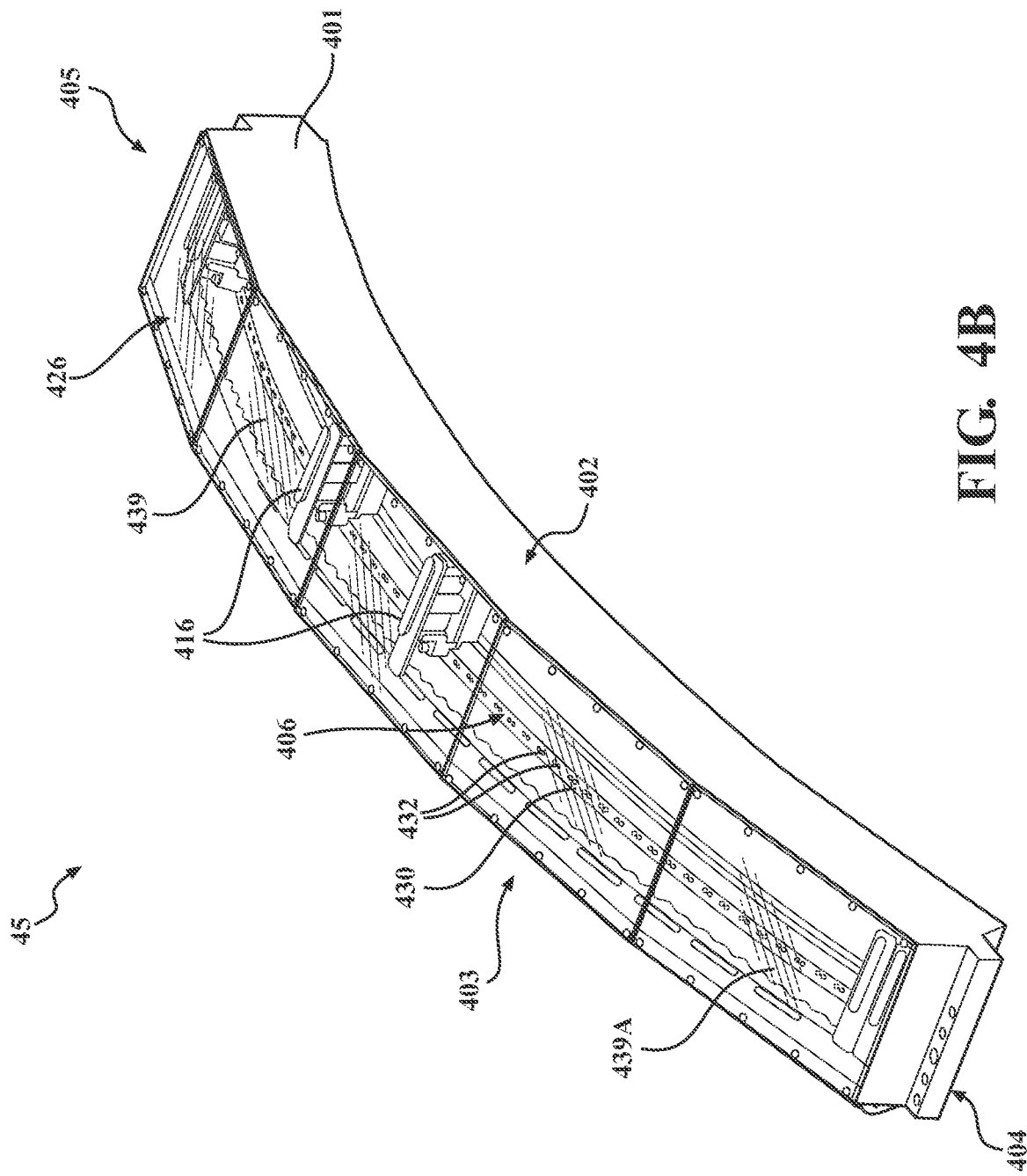

FIGS. 4A-4G illustrate an embodiment of a detector system 45 that may be utilized in an x-ray imaging system, such as the systems 100, 200 described above in connection with FIGS. 1-3. The detector system 45 may include a chassis 401 that may be mounted within the gantry 40 of the imaging system, and in particular, may be mounted to the rotor 41 opposite an x-ray source 43, as shown in FIG. 3. The chassis 401 may comprise a rigid frame comprised of a suitable structural material (e.g., aluminum), and may include a pair of parallel side walls 402, 403 and a pair of end walls 404, 405 defining an interior housing 406 (see FIG. 4B) of the chassis 401. The chassis 401 may have a curved or angled shape along its length dimension, as shown in FIGS. 4A-4B. In embodiments, the chassis 401 may have a length of up to about 1 meter or more (e.g., 1.0-1.5 meters, such as 1.1 meter), a width of at least about 15 cm (e.g., 15-40 cm, such as ~20 cm), and a depth between a front side 407 and a rear side 409 of the chassis 401 that may be between about 10-15 cm.

A plurality of x-ray sensitive detector elements may be located within the interior housing 406 of the chassis 401. In various embodiments, the individual detector elements may be located on a plurality of detector modules 410 (see FIGS. 4C-4F). Each individual detector element 411, which may be for example, a scintillator material coupled to a photodiode, represents a pixel on a multi-element detector module 410. The modules 410 may be 2D element array, with for example 640 pixels per module (e.g., 32×20 pixels), although a greater or lesser number of pixels may be located on a module 410. The pixel pitch of a module 410 may be less than 2 mm, such as about 1 mm (e.g., 0.7-1.3 mm). The detector elements 411 may be arranged in a planar array on the module 410. In other embodiments, the detector elements 411 may be arranged in a non-planar (e.g., curved) array on the module. Each module 410 in a detector system 45 may have a uniform size and shape or the modules 410 may have varying sizes and/or shapes.

Figure 4C:
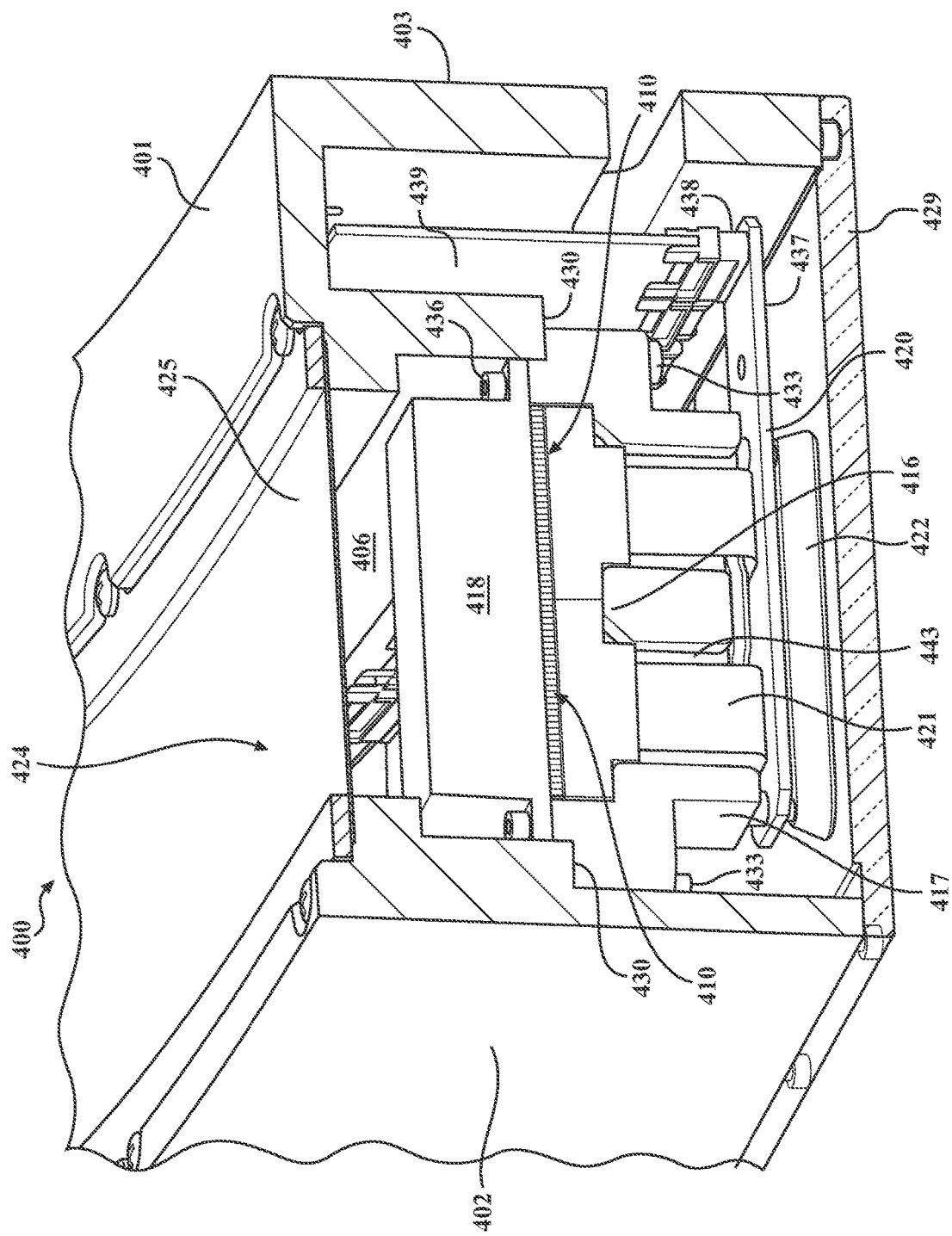
Figure 4D:
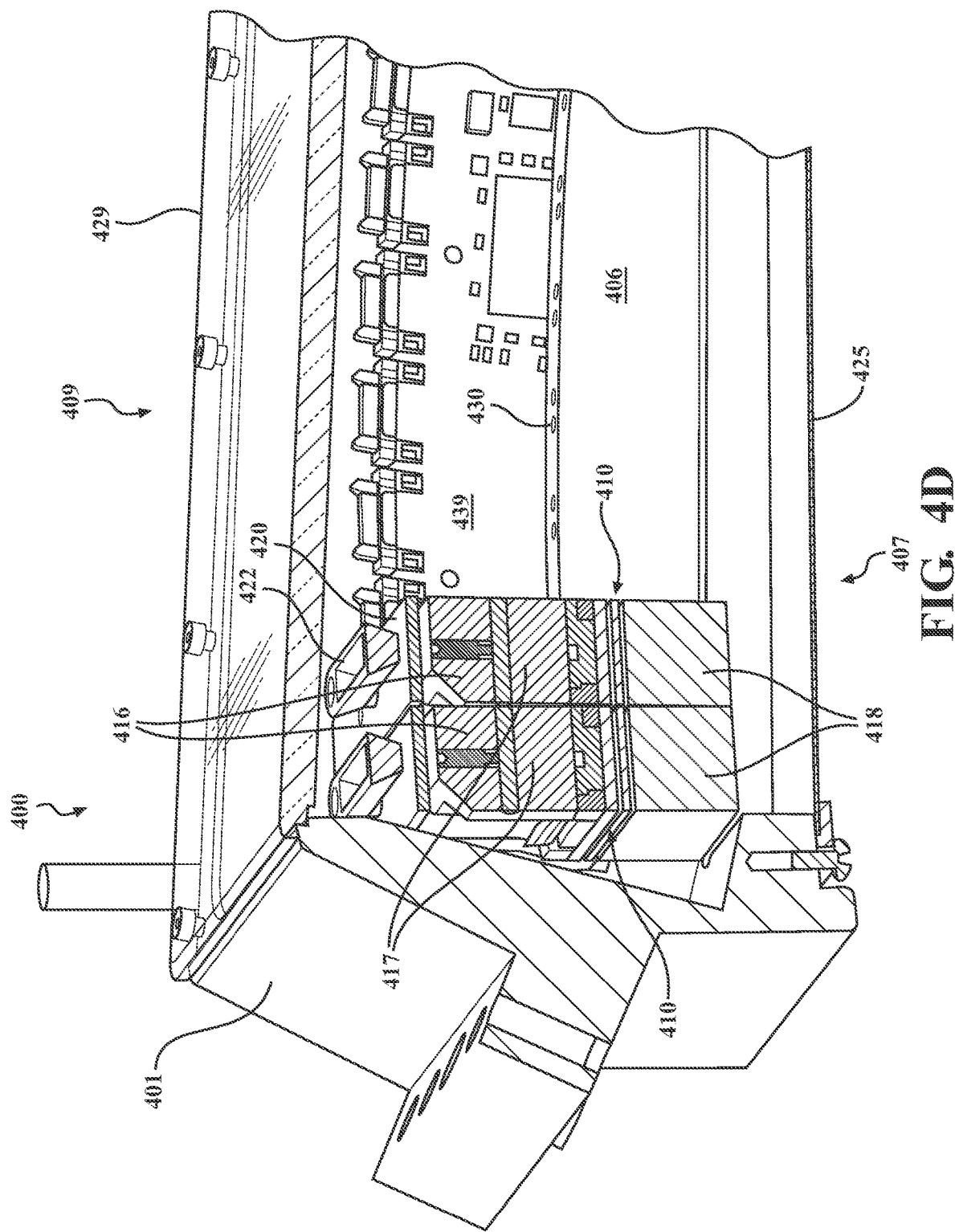
Figure 4E:
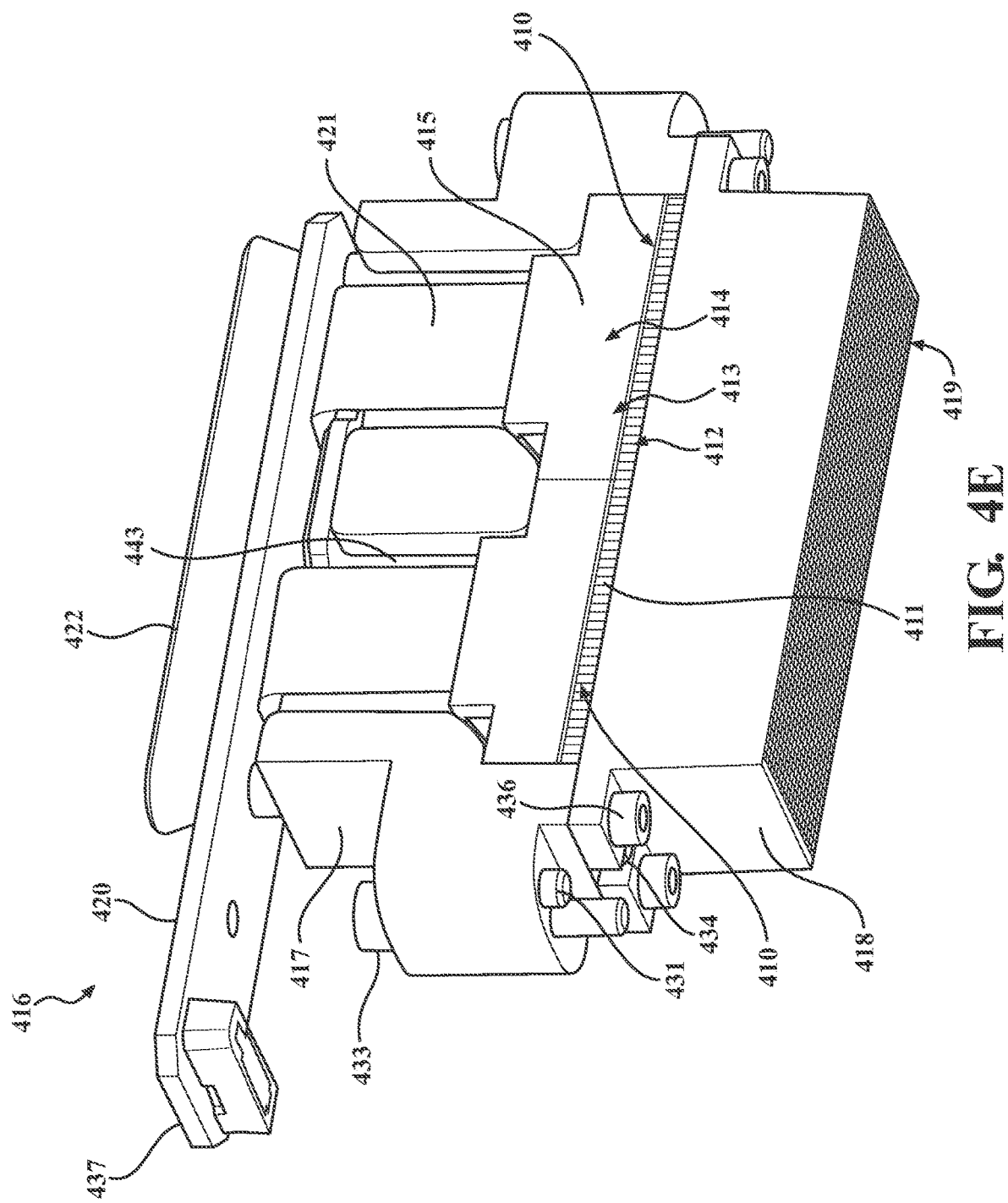
Figure 4F:
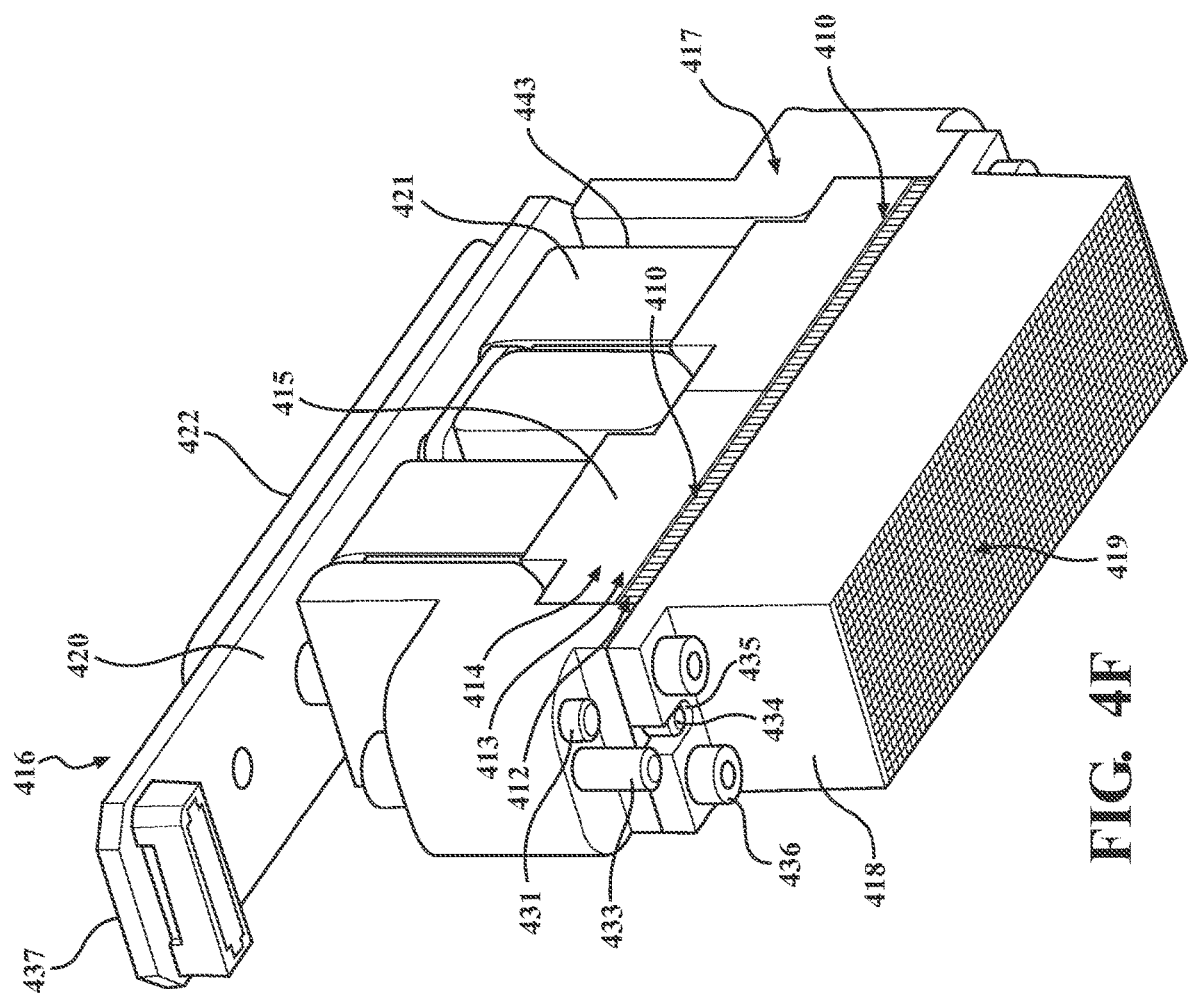

FIGS. 4E and 4F illustrate a pair of detector modules 410. Each module 410 includes a layer of scintillator material 412, such as gadolinium oxysulfide (GOS), a photodiode array 413 optically coupled to the scintillator material 412, and a front-end electronics assembly 414 coupled directly behind photodiode array. The electronics assembly 414 may include analog-to-digital (A/D) converter circuitry for converting the output signals from the photodiode array to digital signals. The signals may comprise a digital representation of an intensity of x-ray photons incident on each individual detector element 411 (i.e., pixel) of the array. The electronics assembly 414 may be closely coupled to the photodiode array in order to minimize signal path length and signal path length differences among the pixels of the detector module 410. This may help minimize noise and increase SNR of the detector module 410. The electronics assembly 414 may be enclosed within a protective housing 415 as shown in FIGS. 4E and 4F.

A plurality of modules 410 may be arranged in an abutting fashion to provide a detector area with a desired size and shape. For example, a plurality of modules 410 may be abutted along the width dimension of the detector system 45 (i.e., parallel to the imaging axis 114 of the gantry 40) to provide an arbitrary number of "slices" that may be imaged simultaneously during a rotation of the rotor 41. The number of slices of the detector system 45 may be, for example, 32 slices, 40 slices, 64 slices, 128-320 slices, etc. In the embodiment shown in FIGS. 4E and 4F, two detector modules 410, each 32 pixels in width, are abutted side-by-side within the detector chassis 401 to provide a 64 slice CT detector system 45. The gap between adjacent modules 410 in the width direction may be less than 0.5 mm, such as less than 0.05 mm (e.g., 0.001-0.05 mm), and may be, for example, between 0.01 and 0.02 mm.

The modules 410 may also be abutted in the transverse direction (i.e., along the length of the chassis 401) to provide a detector area having an arbitrary length. The gap between adjacent modules in the length direction may be less than 1 mm, such as less than 0.5 mm (e.g., 0.01-0.5 mm), and may be, for example, between 0.4 and 0.5 mm. In the detector system 45 of FIGS. 4A-4G, the detector system 45 may include two adjacent rows of detector modules 410, each row being 55 modules in length, for a total of 110 modules. The modules 410 may be curved or angled along the length of the detector chassis 401 to form or approximate a semi-circular arc, with the arc center coinciding with the focal spot 307 of the x-ray source 43 (see FIG. 3). For example, each of the modules 410 may comprise a planar, 2D pixel array that is mounted within the housing 406 of the chassis 401 such that a ray extending from the focal spot 307 of the x-ray source 43 is perpendicular to the surface of the module 410 at the center pixel of the module 410.

The detector system 45 may include a plurality of sub-assemblies 416, each including one or more detector modules 410, where the sub-assemblies 416 may be individually mounted within and removed from the detector chassis 401. FIG. 4B is a rear view of a detector system 45 showing a plurality of sub-assemblies 416 mounted to the detector chassis 401. FIG. 4C is a cross-section view of the detector system 45 (viewed along the width dimension of the detector system 45) showing a sub-assembly 416 mounted to the detector chassis 401. FIG. 4D is another partial cross-section view of the detector system 45 (viewed along the length dimension of the detector system 45) showing a pair of adjacent sub-assemblies 416 mounted to the detector chassis 401. FIGS. 4E and 4F are perspective views of a sub-assembly 416. The sub-assembly 416 in this embodiment includes a support 417 that is configured to receive a pair of adjacent detector modules 410 on a first side of the support 417. The support 417 may comprise a structural material (e.g., aluminum) that preferably has a relatively high thermal conductivity (e.g., ≥200 W/(m·K)). The support 417 may function as a heat sink to facilitate removal of heat from the modules 410, and in particular from the electronics assembly 414 of the modules 410. In embodiments, a thermal paste may be provided at the interface between the detector modules 410 and the support 417. The detector modules 410 and the support 417 may have alignment features that enable the precise positioning of the modules 410 on the support. For example, the modules 410 may include one or more pins that may be received in precision-formed hole(s) in the mating surface of the support 417. Although the sub-assembly 416 shown in FIGS. 4E and 4F supports two detector modules 410, it will be understood that a sub-assembly 416 may support a single detector module 410 or more than two detector modules 410. The sub-assembly 416 may support a plurality of modules 410 such that they form a single planar surface, such as shown in FIGS. 4E and 4F, or may support the modules 410 such that they are angled relative to one another (e.g., such as to approximate an arc centered on the focal spot 307 of the x-ray source 43).

The sub-assembly 416 may also include an anti-scatter assembly 418 attached to the support 417 over the detector modules 410. The anti-scatter assembly 418 may comprise a grid 419 made from an x-ray absorbent material, such as tungsten or lead, having openings aligned over the pixels of the detector modules 410. The x-ray absorbent material of the grid 419 may be located between adjacent columns and rows of detector elements (pixels) of the module 410 so as to inhibit scattered x-rays, traveling at an oblique angle, from impinging on the detector elements. The anti-scatter assembly 418 may be provided so that the detector elements primarily measure the intensity of x-rays that travel along a straight-line path from the x-ray source 43 to the detector 45. The anti-scatter assembly 418 may comprise a focused grid having apertures that are angled toward the focal spot of the x-ray source. Although the anti-scatter assembly 418 in this embodiment is a two-dimensional grid 419 located between each column and row of detector elements, it will be understood that other configurations can be utilized, including an array of x-ray absorbent plates located between adjacent columns or rows of detector elements to absorb scattered x-rays along one direction.

The sub-assembly 416 may also include at least one electronics board 420 attached to a second side of the support 417 that is opposite the first side to which the module(s) 410 are attached. One or more electronic cables 421 may extend between each of the modules 410 and the electronics board 420. As shown in FIGS. 4E and 4F, a pair of ribbon cables 421 extends between the electronics assemblies 414 of the modules 410 and the electronics board 420. The cables 421 may extend in recessed portions 443 (e.g., grooves) extending along the side of the support 417 that are sized and shaped to accommodate the cables 421, as shown in FIGS. 4E and 4F. The cables 421 may provide power from the electronics board 420 to each of the modules 410. The cables 421 may also carry image data (e.g., digital x-ray attenuation data) from the modules 410 to the electronics board 420. The electronics board 420 may include memory and at least one processor (e.g., an FPGA) programmed to receive digital image data from the electronics assemblies 414 of the detector modules 410, and assemble the data into a single image. The detector system 45 may include a "double buffering" configuration, such that while a first plurality (e.g., frame) of image data accumulates in a first buffer, a second plurality (e.g., frame) of digital image data may be read out from a second buffer. The data from the first buffer may then be read out while new data accumulates in the second buffer, and so on. The detector modules 410 may continually collect digital image data while the detector 45 is continuously exposed by the x-ray source 43. In some embodiments, the electronics assemblies 414 of the detector modules 410 may transmit the image data in a digital video format, such as LVDS. The at least one processor on the electronics board 420 may be configured to convert the image data to a different digital video format, such as Camera Link or gigabit Ethernet.

The electronics board 420 may be secured to the support 417 of the sub-assembly 416 using an adhesive and/or suitable fastener(s). A handle 422 or other element to enable the sub-assembly 416 to be easily gripped and manipulated may be located over the electronics board 420 opposite the support 417. One or more fasteners (e.g., screws) may extend through the handle 422 and the electronics board 420 and into the support 417 to clamp the electronics board 420 to the support 417.

As shown in FIGS. 4A and 4C, the front side 407 of the detector chassis 401 may include an open window region 424 over the detector modules 410. A cover 425 made of a material that is x-ray translucent but opaque to visible radiation (e.g., a thermoplastic material, carbon fiber, etc.) may be mounted to the front side 407 of the detector chassis 401 over the plurality of detector modules 410. The rear side 409 of the detector chassis 401 may include a plurality of access openings 426, as shown in FIG. 4B. A plurality of access panels may be secured over the openings 426. FIG. 4C illustrates an access panel 429 in phantom. The access panels 429 may include interlocking features to prevent ambient light from entering the detector system 45.

As shown in FIGS. 4B, 4C and 4D, a pair of lip portions 430 may extend along the interior sidewalls of the housing 406 of the detector chassis 401. The lip portions 430 may have a curved or faceted profile over the length of the chassis 401, as shown in FIG. 4B, so that when the detector sub-assemblies 416 are mounted to the chassis 401 the detector modules 410 are arranged in a generally semicircular arc configuration along the length of the chassis 401. Each of the detector sub-assemblies 416 may include one or more alignment pins 431 (see FIGS. 4E and 4F) for aligning the sub-assembly 416 within the detector chassis 401. The alignment pins 431 may be received in openings 432 on the lip portion(s) 430 of the chassis 401 (see FIG. 4B). A set of fasteners 433 (e.g., screws) may be inserted through the support 417 and into the respective lip portions 430 to secure the sub-assembly 416 to the chassis 401. A plurality of sub-assemblies 416 may be mounted to the lip portions 430 of the detector chassis 401. FIG. 4B illustrates six sub-assemblies 416 mounted to the chassis 401. It will be understood that a detector system 45 may include a series of sub-assemblies 416 (e.g., 55 sub-assemblies) mounted adjacent to one another along the length of the chassis 401.

The support 417 of the sub-assembly 416 may also include a set of alignment pins 434 to facilitate alignment of the anti-scatter assembly 418 over the detector modules 410. The alignment pins 434 may be received in a recessed portion 435 of the anti-scatter assembly 418, as shown in FIGS. 4E and 4F. A set of fasteners 436 (e.g., screws) may be inserted through the anti-scatter assembly 418 and into the support 417.

In embodiments, to access the detector modules 410 and/or electronics boards 420 for service and/or replacement, one or more access panels 429 may be removed from the rear side 409 of the detector chassis 401, and an individual sub-assembly 416 may be disconnected and removed from the detector chassis 401 without disturbing other sub-assemblies 416 of the detector system 45.

In the embodiment shown in FIGS. 4B-4F, the electronics board 420 of each sub-assembly 416 may include a cantilevered end 437 that projects out from the side of the sub-assembly 416. The cantilevered end 437 may include a connector 438 (e.g., plug) that connects to an additional circuit board 439 (e.g., a motherboard) extending on the periphery of the detector system 45 (e.g., between the lip portion 430 and the side wall 403 of the detector chassis 401). Alternately, the electronics board 420 of the sub-assembly 416 may connect to the additional circuit board 439 via a cable connection (e.g., a ribbon cable). The additional circuit board 439 may extend perpendicular to the electronics board 420 and parallel to side wall 403 of the detector chassis 401. The additional circuit board 439 may be connected to a plurality of sub-assemblies 416 (e.g., at least two sub-assemblies 416, and in some embodiments, all of the sub-assemblies 416 of the detector 45). Connectors 438 between each of the electronics boards 420 and the additional circuit board 439 may be utilized to provide power to the electronics boards 420 and to receive data (e.g., digital x-ray data) from each of the electronics boards 420. The additional circuit board 439 may include memory and at least one processor (e.g., an FPGA) programmed to receive digital image data from the sub-assemblies 416 and to combine and assemble the data into a single image. In embodiments, electronics boards 420 may be data acquisition system (DAS) boards that may provide circuit integration and the transfer of data from the electronics modules 410 to a motherboard (e.g., board 439).

Figure 4G:
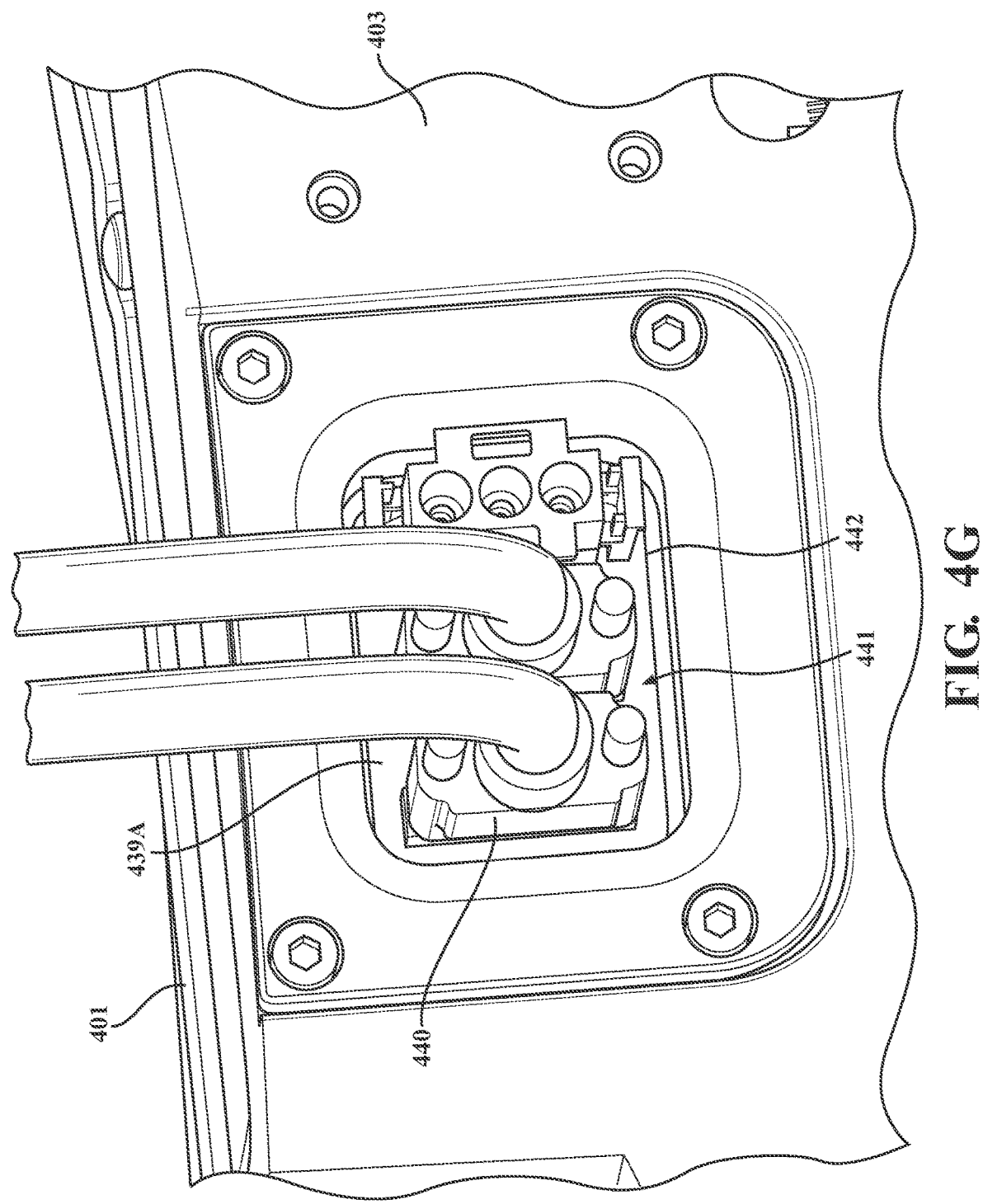

The detector system may include a plurality of additional circuit boards 439 that may extend along the length of the detector chassis 401. FIG. 4B illustrates four circuit boards 439 extending along the length of the chassis 401, although it will be understood that a greater or lesser number of boards may be utilized. Each of the additional circuit boards 439 may receive and combine digital image data from a group of sub-assemblies 416 to generate a combined dataset. The additional circuit boards 439 may be connected to one another in a daisy-chain fashion such that each board 439 may combine its own image dataset with an image dataset received from a preceding board 439 in the chain. The resulting combined dataset may then be transmitted to a subsequent board 439 which may repeat this process so that the image data is propagated down the line to a final board of the chain (e.g., board 439A in FIG. 4B). The final board 439A may include one or more external connectors or ports 440 (see FIG. 4A) for receiving power from a suitable power supply (e.g., a battery system 63 as shown in FIG. 3) and for transmitting the combined image dataset to an external device (e.g., computer 46 as shown in FIG. 3) for performing processing operations, including tomographic reconstruction. FIG. 4G is an enlarged view of an interface between the detector system 45 and a plurality of external connectors 440. As shown in the enlarged view of FIG. 4G, the external connectors 440 may plug directly into a circuit board 439A of the detector system 45. The side wall 403 of the detector chassis 401 may include an opening 441 to enable the connector(s) 440 to connect to the circuit board 439A. A compliant member 442 (e.g., gasket) may surround the opening 441 between the chassis side wall 403 and the circuit board 439A.

In embodiments, the detector chassis 401, including at least the side walls 402, 403, end walls 404, 405 and lip portions 430 to which the detector sub-assemblies 416 are mounted, may be formed (e.g., precision machined) from a single workpiece (e.g., an aluminum block). This may improve the manufacturability of the detector system while ensuring that required tolerances are met.

The detector chassis 401 may be made from a material having a relatively high thermal conductivity (e.g., $\geq 200$ W/(m·K)), such as aluminum. Cooling of the interior housing 406 of the detector chassis 401 may be primarily through conduction. As discussed above, each of the sub-assemblies 416 of the detector may include a support 417 that functions as a heat sink to conduct heat away from the detector modules 410 and other electrical components. The sub-assemblies 416 are mechanically and thermally coupled to the detector chassis 401 (i.e., at the interface between the support 417 and the lip portions 430 of the chassis 401) so that heat is conducted from the sub-assemblies 416 into the chassis 401. The supports of the sub-assemblies and the chassis walls may provide a thermally-conductive path from the detector modules 410 and electronics boards 420 to the exterior surfaces of the chassis 401. In embodiments, a thermal paste may be provided at the interface between the sub-assemblies 416 and the chassis 401. Other heat generating components of the detector system 45, such as a power supply and the additional circuit board(s) 439, may be directly mechanically and thermally coupled to the chassis 401, such as fastened to the interior side wall 403 of the chassis 401. A cooling fluid (e.g., air) may be directed through the interior of the gantry 40 and over the exterior surface of the detector chassis 401 to cool the detector system 45.

Alternately or in addition, the detector system 45 may include a cooling system for directing a cooling fluid (e.g., air) through the interior housing 406 of the detector chassis 401 to remove heat, such as described in U.S. Pat. No. 9,125,613, the entire contents of which are incorporated by reference herein.

The heat load of the detector system 45 may also be managed by controlling the power provided to the detector system 45 (e.g., from batteries 63) so that all or a portion of the electrical components of the detector system 45 may remain unpowered or minimally powered when not in use. A control system (e.g., controller 113) may maintain the detector system 45 in an unpowered or low-power "standby" mode until the imaging system is ready to perform an imaging scan. Upon initiation of a scan, the control system may transmit a control signal to cause the detector system 45 to be powered up to an operational mode in which the detector system 45 is ready to obtain x-ray image data. After the scan is complete, the detector system 45 may be returned to an unpowered or low-power standby mode until the next scan is initiated.

In an alternative configuration of the detector system 45, the electronics boards 420 of the sub-assemblies 416 may be directly connected to one another, such as via a plurality of ribbon cables. Additional circuit board(s) 439 extending along the length of the chassis 401 may optionally be omitted. The electronics boards 420 of the plurality of sub-assemblies 416 may transmit the collected image data along a series of adjacent sub-assemblies 416 in a daisy chain configuration, such as described in U.S. Pat. No. 9,111,379, the entire contents of which are incorporated by reference herein. Each sub-assembly 416 may combine its own image data with the image data received from a preceding sub-assembly 416, and transmit the combined image data to the next sub-assembly 416 in the series. The combined image dataset from all of the sub-assemblies 416 may be streamed into a frame grabber (e.g., where the data may be converted to gigabit Ethernet format) and the frames of data may be streamed into an external processing device (e.g., computer 46) for performing tomographic reconstruction and/or other processing operations.

In some embodiments, at least a portion of the image data processing operations, including tomographic reconstruction, may be performed within the detector system 45 itself. In embodiments, at least one image processing/reconstructor module may be located within the detector system 45. The image processing/reconstructor module may be implemented on a separate computer located on or within the detector chassis 401 and/or on one or more circuit boards 439 within the detector chassis 401. The image processing/reconstructor unit may comprise a parallel processor having a plurality of processing cores for performing the tomographic reconstruction process in parallel. For example, the parallel processor may be a graphics processing unit (GPU), and may be located on a graphics card. The GPU may include a large internal memory (e.g., up to 8 gigabytes or more, such as 2-4 gigabytes) and a plurality of processing cores (e.g., up to 4096 cores or more, such as 2048 cores) for performing parallel processing of the image data. It will be understood that the image processing/reconstructor module may be implemented using any suitable processing device, such as one or more of a GPU, a CPU, an FPGA, ASIC, etc. The image processing/reconstructor module may receive inputs of encoder position(s) (e.g., indicating the rotation position of the rotor 41 and/or translation/rotation of the gantry 40), source-to-detector distance, x-ray photon flux and/or x-ray source temperature (e.g., from a reference detector as described in U.S. Pat. No. 9,111,379). The image processing/reconstructor module may be configured to perform various image correction techniques on the image data, such as offset correction, gain correction and/or pixel correction. In some embodiments, the image processing/reconstructor module may also perform other real-time processing operations (e.g., for 2D fluoroscopy), including edge enhancement, recursive noise reduction and super resolution techniques as described below.

Figure 5A:
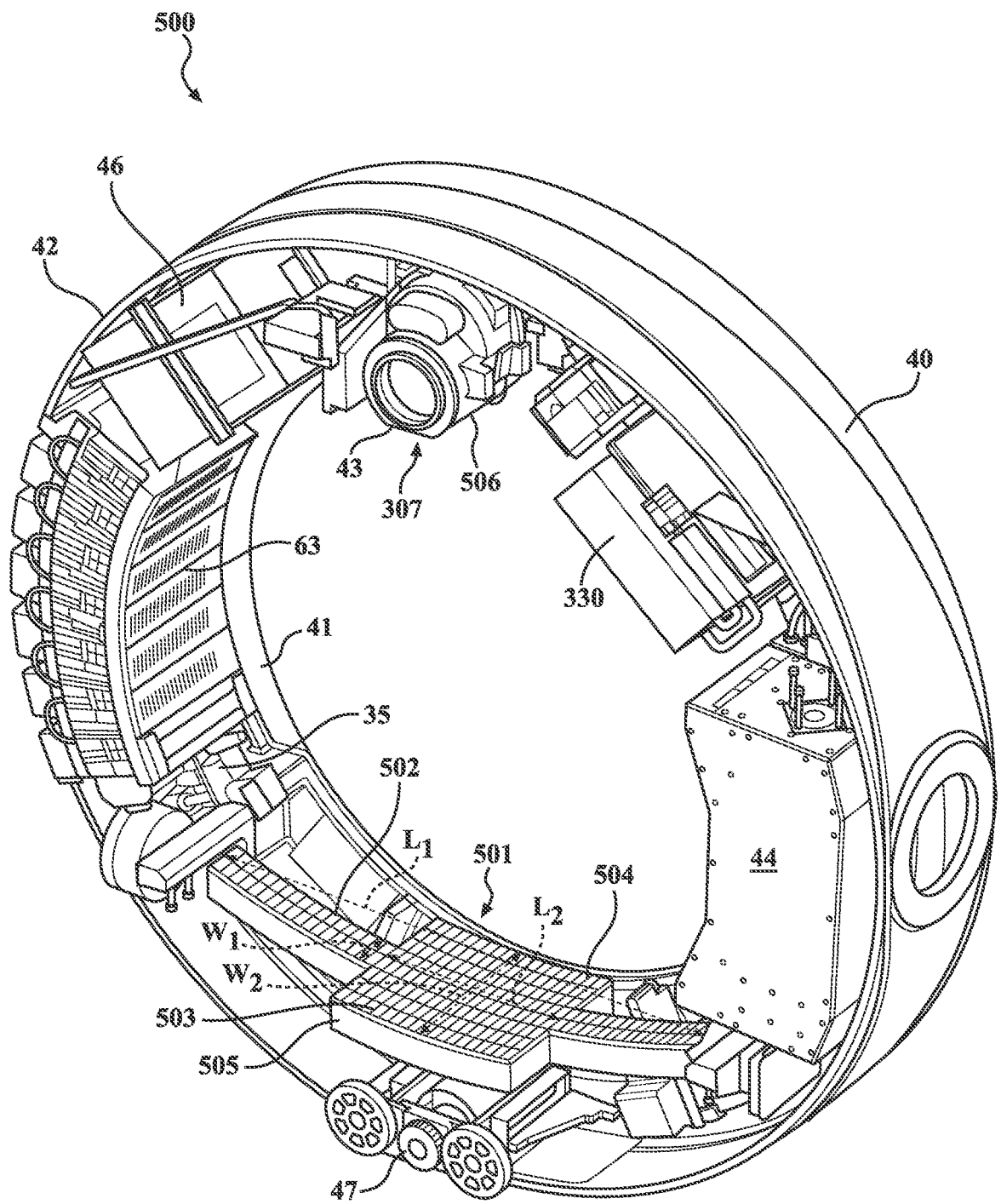
FIGS. 5A-5C illustrate a hybrid x-ray imaging system for performing fan- and cone-beam CT imaging and 2D fluoroscopy.
Figure 5B:
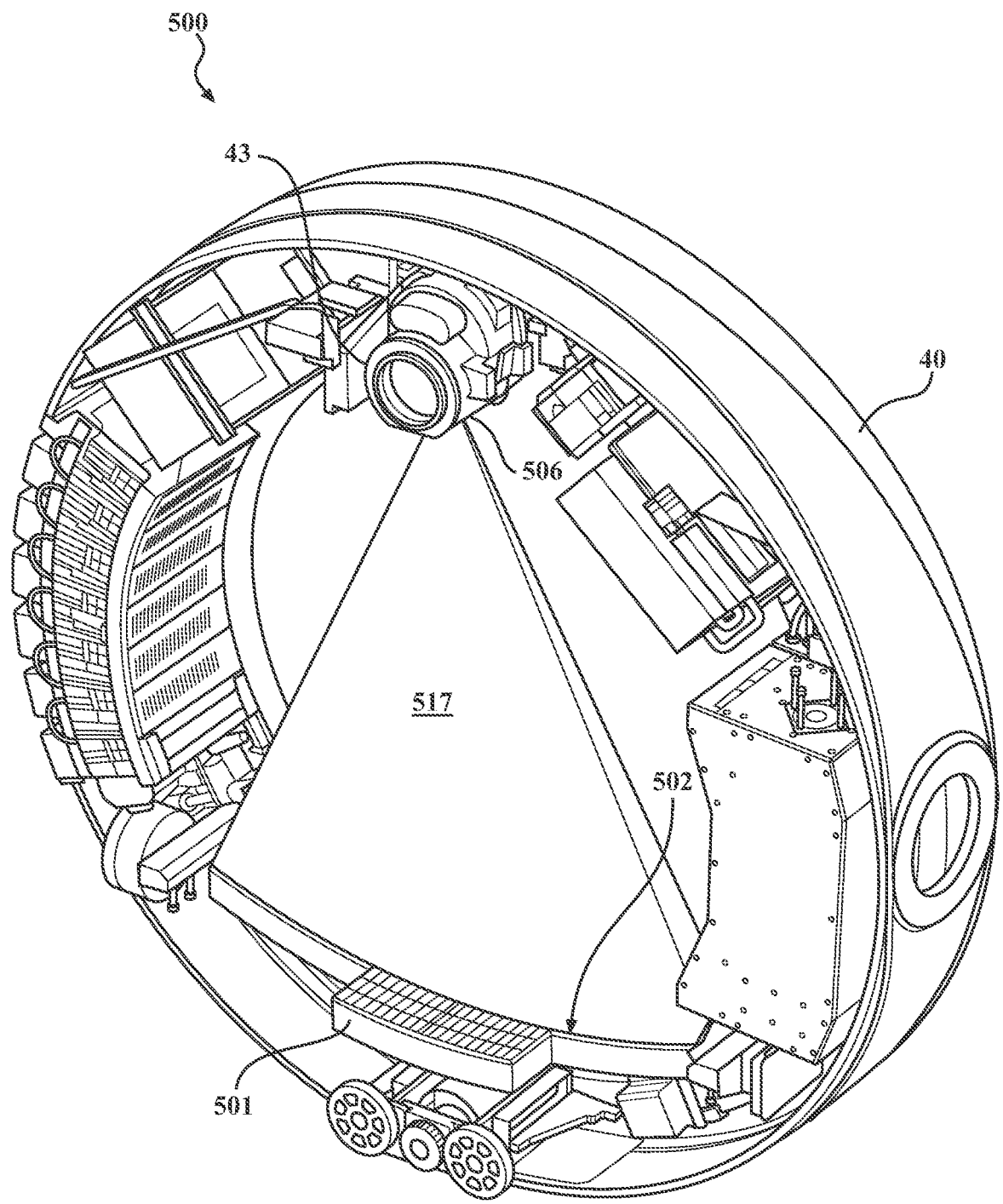
Figure 5C:
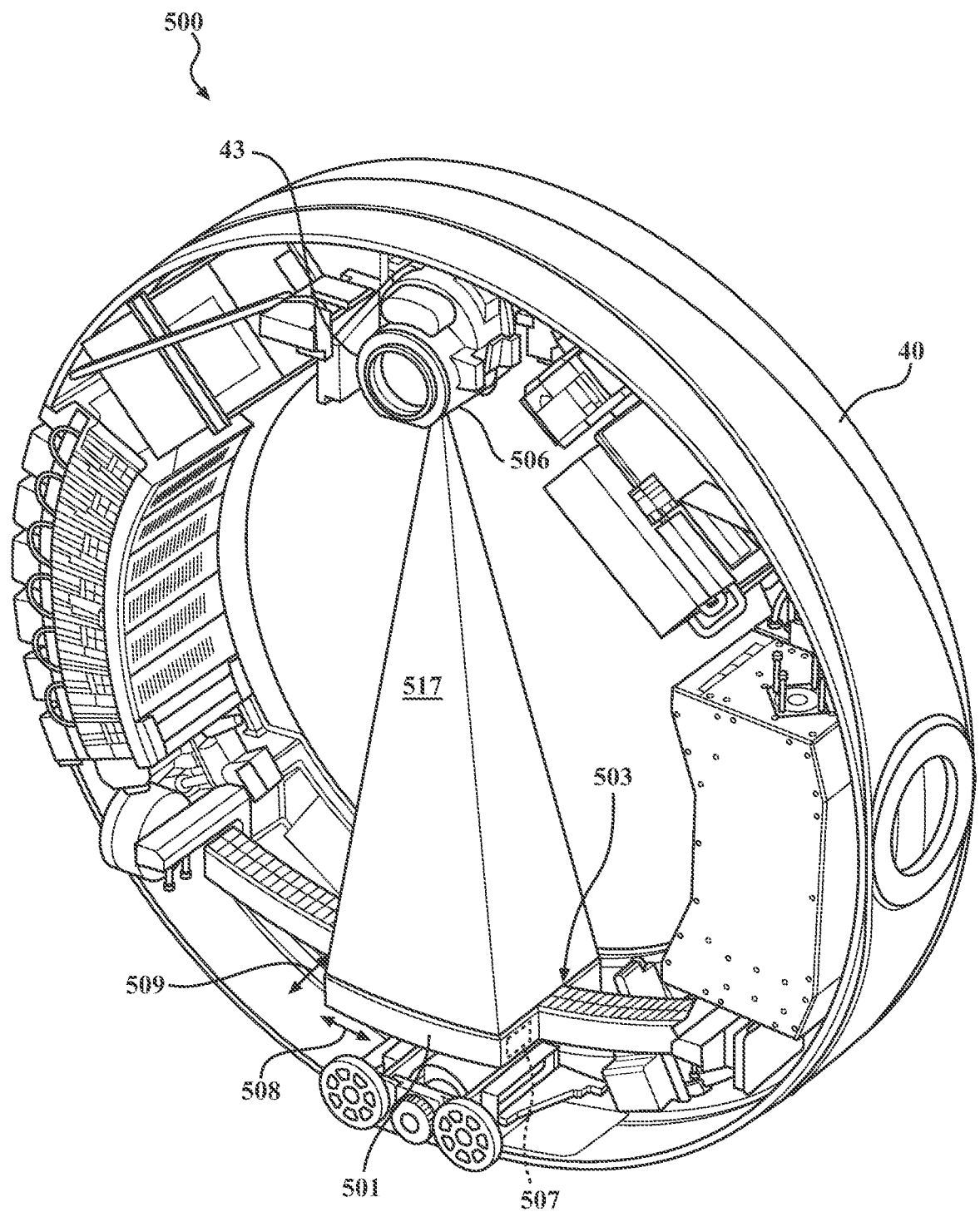

FIGS. 5A-5C illustrate another embodiment imaging system 500 that may be used for both 3D CT imaging and 2D fluoroscopic imaging. FIG. 5A is a cross-section view of a gantry 40 of an imaging system 500, which may be similar to systems 100, 200 shown in FIGS. 1 and 2. The gantry 40 includes a rotor 41 that is mounted to and rotates within an outer shell 42 of the gantry 40. A plurality of components, including an x-ray source 43, a high-voltage generator 44, a heat exchanger 330, an x-ray detector system 501, a power supply 63 (e.g., battery system), a computer 46, a rotor drive mechanism 47, and a docking system 35, may be mounted to the rotor 41 as described above.

The detector system 501 in this embodiment is a hybrid detector system having a contiguous detector area that includes an elongated first portion 502 for performing fan-beam CT imaging (e.g., axial and/or helical scans) and a panel-shaped second portion 503 for performing 2D fluoroscopic imaging and/or 3D cone beam CT imaging. The first portion 502 and the second portion 503 may be overlapping, such that a portion of the detector area is shared by both the first portion 502 and the second portion 503. The first portion 502 may have a length dimension (L1) that is greater than the length dimension (L2) of the second portion 503. For example, the first portion 502 may have a length that is greater than 0.5 meter, such as 1 meter or more, and the second portion 503 may have a length that is less than 0.5 meter, such as between about 0.3 and 0.4 meters. The second portion 503 may have a width dimension (W2) that is greater than the width dimension (W1) of the first portion 502. For example, the first portion 502 may have a width that is less than 0.3 meters (e.g., 0.15-0.25 meters) and the second portion 503 may have a width that is greater than 0.3 meters (e.g., 0.3-0.4 meters or more).

The detector area may be produced by arranging an array of detector modules 504 in a desired geometric shape or pattern. The modules 504 may be similar or identical to the modules 410 described above with reference to FIGS. 4A-4G. For example, each module 504 may include an array of individual detector elements (pixels), each including a scintillator (e.g., GOS) coupled to a photodiode, and including an electronics assembly for outputting digital image data. The modules 504 may be abutted along any of their edges to form a detector area having any arbitrary size and shape. In the embodiment of FIGS. 5A-5C, the first portion 502 of the detector area may be formed by abutting a group of modules 504 along the length dimension, L1, and the width dimension, W1. For example, the first portion 502 may include two adjacent rows of detector modules 504, each row being 55 modules in length, for a total of 110 modules, similar to the detector system 45 shown in FIGS. 4A-4G. The first portion 502 may be a large field-of-view (e.g., providing ~50 cm diameter or greater reconstruction volume), multi-slice (e.g., 64 slice) true CT detector.

The second portion 503 of the detector area may be formed by abutting additional row(s) of modules 504 in the width direction along a section of the modules 504 forming the first portion 502. In the embodiment of FIGS. 5A-5C, the second portion 503 of the detector area may be formed by abutting three additional rows of modules 504 on either side of a central section of the two rows of modules 504 forming the first portion 502. The length of the central section may define the length dimension, L2, of the second portion 503. The distance between the edges of the outer two rows of modules 504 in the second portion 503 may define the width dimension, W2, of the second portion 503. In the embodiment of FIGS. 5A-5C, the second portion 503 of the detector area includes eight adjacent rows of detector modules 504, each row being nineteen modules in length, for a total of 152 modules. The second portion 503 may be a rectangular panel detector that may be used for 2D x-ray fluoroscopy and/or cone-beam CT imaging.

The detector modules 504 in the detector system 501 may have a uniform size and shape or may have varying size(s) and/or shape(s). In one embodiment, the modules 504 may be a 2D element array, with for example 640 pixels per module (e.g., 32×20 pixels). The modules 504 may be mounted within a housing of a detector chassis 505, which may be similar to the chassis 401 shown in FIGS. 4A-4D. In FIGS. 5A-5C, the chassis 505 is schematically illustrated supporting the array of detector modules 504. In embodiments, the chassis 505 may enclose the modules 504 within an internal light-tight housing (not illustrated in FIGS. 5A-5C for clarity). The chassis 505 may be sized and shaped to accommodate the first and second portions 502, 503 of the detector area.

The modules 504 may be supported on the chassis 505 such that the modules 504 are curved or angled along the length of the chassis 505 to form or approximate a semicircular arc, with the arc center coinciding with the focal spot 307 of the x-ray source 43 (see FIG. 3). In some embodiments, the modules 504 of the second portion 503 may additionally be curved or angled along the width of the chassis 505 to form or approximate a semicircular arc centered on the focal spot 307 of the x-ray source 43. The modules 504 of the second portion 503 may thus approximate a portion of a spherical surface that is centered on the focal spot 307 of the x-ray source 43.

Each detector module 504 may be electronically coupled to an electronics board (e.g., similar or identical to the electronics board 420 shown in FIGS. 4B-4G) that provides power to the module 504 and receives digital image data from the module 504. The detector system 501 may include a plurality of electronics boards that are arranged behind the detector modules 504 within the chassis 505. Each electronics board may be electrically connected to more than one detector module 504. The electronics boards may have a uniform size and shape and may be connected to the same number of detector modules 504. Alternately, the electronics boards may have different sizes and shapes and may be connected to different numbers of detector modules 504. For example, the electronics boards of the first portion 502 of the detector system 501 may each connect to a first number of detector modules 504 (e.g., 2 modules, such as in the embodiment of FIGS. 4A-4G), and the electronics boards located behind the peripheral rows of the second portion 503 of the detector system 501 may each connect to a different number of detector modules 504 (e.g., greater than 2 modules, such as 3-10 modules). Each of the electronics boards may send the image data received from the detector modules 504 to a processing unit (e.g., an FPGA) that may be configured with software to unscramble the data and assemble a combined image dataset (e.g., image frame) from all of the detector modules 504 in a selected area that is exposed to x-ray radiation.

In embodiments, the detector system 501 may include a plurality of sub-assemblies that may be individually mounted within and removed from the detector chassis 505. The sub-assemblies may be similar or identical to the sub-assemblies 416 shown in FIGS. 4B-4F and may include a support that is mounted to the detector chassis 505, where the support includes one or more detector modules 504 and one or more electronics boards attached thereto. In one non-limiting example, a first group of sub-assemblies forming the elongated, narrower "wing" sections of the first portion 502 (i.e., that do not overlap with the second portion 503) may be identical to the sub-assemblies 416 described above in connection with FIGS. 4B-4F. A second group of sub-assemblies may be mounted within the chassis 505 to form the second portion 503 of the detector system 501. Each of the second group of sub-assemblies may include a greater number of detector modules 504 (e.g., eight modules) attached to a support that extends across the width of the detector system 501. Alternately, the chassis 505 may include a plurality of support ribs extending within the second portion 503 of the second portion 503 of the detector to which the sub-assemblies may be attached.

The detector system 501 may also include an anti-scatter assembly located over the detector modules 504. The anti-scatter assembly may include a two-dimensional grid comprised of x-ray absorbent material located between the columns and rows of detector elements (pixels) or may be an array of x-ray absorbent plates located between adjacent columns or rows of detector elements. The anti-scatter assembly may include grid or plate elements mounted above the detector modules in each sub-assembly of the detector system 501, as shown in FIGS. 4C-4F.

In embodiments, the x-ray source 43 of the imaging system 500 may include an adjustable collimator 506 that defines the shape of the x-ray beam 517 emitted by the source 43. The collimator 506 may include motor-driven shutters or leaves comprised of an x-ray absorbent material (e.g., lead or tungsten) that may block a portion of the x-rays generated by the x-ray tube. In a first configuration shown in FIG. 5B, the collimator 506 may collimate the beam 517 so that it covers the first portion 502 of the detector area. In a second configuration shown in FIG. 5C, the collimator 506 may collimate the beam 517 so that it covers the second portion 503 of the detector area. The first configuration shown in FIG. 5B may be utilized, for example, for performing large field-of-view fan-beam helical or axial CT scans. The second configuration shown in FIG. 5C may be utilized for performing 2D fluoroscopic imaging and/or 3D cone-beam CT scans. In embodiments, the configuration of the collimator 506 may be adjusted by a system controller, which may be implemented on a computer (e.g., computer 46). The system controller may also send a configuration signal to the detector system 501 to indicate the detector modules 504 from which to read out image data based on the shape of the x-ray beam 517. The imaging system 500 as shown in FIGS. 5A-5C may be used to perform diagnostic-quality CT scans (e.g., multi-slice large field-of-view axial and/or helical scans), 2D fluoroscopic imaging and/or 3D cone beam CT imaging using a single x-ray source 43, high-voltage generator 44 and detector system 501.

A detector system 501 such as shown in FIGS. 5A-5C may have advantages over conventional flat-panel detectors that are used for fluoroscopy and cone-beam CT imaging. For example, the detector system 501 may enable continuous exposure to x-ray radiation, which is in contrast with some flat-panel detectors that require pulsing or strobing of the x-ray source and may have a relatively low duty cycle. A detector system 501 according to various embodiments may utilize a double- or multi-buffering system as described above, such that the detector system 501 may continuously collect new x-ray image data while reading out previously-collected image data. The detector system 501 may be used to collect, and optionally display, x-ray image data at a relatively high frame rate (e.g., >30 Hz, such as 60 Hz or greater, and in some cases more than 1000 Hz). An embodiment detector system 501 may also increase the efficiency of the imaging system 500. For example, conventional flat panel detector systems may require high power (e.g., ≥100 kW) generators to produce the required voltage and current within the tube. The reason for this is that the relatively low duty cycle of the detector limits the total dose of x-rays that can be used for each image frame per unit of time. For example, in a pulsed x-ray system with a 30 Hz frame rate but only 300 msec of x-ray exposure per second, in order to obtain 300 mA-seconds of data, one needs to expose at approximately 1000 mA per pulse. However, with a continuous exposure system according to the various embodiments, the tube current may be significantly lower to obtain the equivalent milliamp-seconds (e.g., 300 mA to get 300 mA-seconds). This may enable lower power (e.g., ≤40 kW) generators to be used and can reduce the size and power requirements of the system 500.

A detector system 501 as described above may also provide improved image quality over an equivalent flat panel detector by including a curved profile (in one or two dimensions) in which the detector elements or modules 504 are arranged along an arc centered on the x-ray focal spot, and may also include a 1D or 2D anti-scatter assembly as described above. The detector system 501 may enable diagnostic-quality cone-beam CT images over at least the center slice of the reconstruction. Further, a true CT detector system 501 as described above may have better dynamic range than a conventional flat panel detector used for fluoroscopic imaging.

In embodiments, the rotor 41 containing the x-ray source 43 and the detector system 501 may rotate within the gantry 40 at least 90° per second, including 180°, 270° or 360° or more per second. The rotation of the rotor 41 may be continuous (i.e., the rotor 41 may continuously rotate through 360° in the same direction). The rotation of the rotor 41 may be unidirectional or bi-directional (i.e., in both clockwise and counterclockwise directions). The system controller (e.g., computer 46) may precisely control the rotation and rotational position of the rotor 41 by sending control signals to the rotor drive system 47. The rotor position may be controlled based on encoder feedback data. The rotor components may be completely housed within the gantry 40 during their rotation to avoid any possibility of collision with a person or other object.

In embodiments, the rotor 41 may be controlled to move to different rotational positions to obtain x-ray fluoroscopic images from different projection angles (e.g., anterior-posterior, lateral images). The rotor 41 may rotate between the different projection angles in a short period of time (e.g., 500 msec or less) to provide updated "real time" fluoroscopic images from multiple projection angles.

The imaging system 500 may also be used to obtain 2D and/or 3D CT images along oblique projection angles by rotating/tilting the gantry 40 with respect to the patient (i.e., such that the patient axis is not parallel to the gantry imaging axis 114). For example, a system that is configured as shown in FIG. 1 may enable isocentric rotation of the gantry 40 in a "tilt" direction (i.e., about axis 107) and/or in a "wag" direction (i.e., about axis 102). A system such as shown in FIG. 2 may enable isocentric "tilt" rotation of the gantry 40 (i.e., about axis 207). Isocentric "wag" rotation may be achieved by performing a coordinated pivot motion of the gantry 40 and support column 201 (i.e., about axis 211) and a translation of the gantry 40 and support column 201 (i.e., in the direction of arrow 209) to maintain the isocenter of the gantry in the same location. In embodiments, an imaging system 500 as shown in FIGS. 5A-5C may perform real-time x-ray fluoroscopy in wide number of projection angles, including steep oblique angles. The gantry 40 may also be translated along the patient (by a distance of up to at least about 1 meter) for performing fan-beam or cone-beam CT scans.

Further embodiments include methods and systems for improving the spatial resolution and/or signal-to-noise ratio (SNR) of x-ray images using super resolution (SR). In an imaging system such as the system 500 shown in FIGS. 5A-5C, the spacing of the pixels (i.e., the center-to-center spacing of adjacent pixels in the detector system 501) may define the spatial resolution of the imaging system. For example, a pixel spacing of 1 mm provides a special resolution of 1×1 mm at the detector face. This results in a resolution of about 0.5×0.5 mm at the isocenter of the imaging bore 116 of the system. Thus, a detector system 501 with a pixel spacing of ~1 mm may be used for 2D fluoroscopic or 3D tomographic images having a spatial resolution of about 0.5×0.5 mm.

There is an inherent tradeoff between pixel size and signal-to-noise ratio (SNR) in that the smaller the pixel size, the less photons are incident on each pixel per unit of time and the lower the SNR of the system. Thus, improving the spatial resolution by decreasing the pixel size may lower the SNR of the system below generally acceptable levels. This issue may be partially compensated by, for example, increasing the number of x-ray photons emitted by the source 43 (e.g., by employing a large, high-power (e.g., 120-130 kW) high-voltage generator coupled to the x-ray tube) and decreasing the exposure time (i.e., to maintain approximately the same x-ray radiation dose). However, these approaches may not be feasible due to size and power constraints of the system. Further, there may be an upper limit in terms of the ability of the system's electronics components (e.g., A/D converters, frame grabbers, etc.) to collect large quantities of raw projection data in a relatively short time period. In addition, the power of the x-ray source 43 can only be increased so much until radiation dosing and exposure levels become a safety issue. Thus, for all of these reasons there is generally a practical lower limit on the pixel size of the detector and therefore the achievable spatial resolution in the image.

Various embodiments include methods and systems for improving the spatial resolution of an x-ray imaging system using super-resolution. Embodiments may be implemented in software, and may improve spatial resolution of the image without requiring smaller pixel sizes for the detector. In addition, embodiments may improve the spatial resolution without decreasing the signal-to-noise ratio (SNR) of the detector. Further embodiments may improve the spatial resolution while maintaining or even decreasing the x-ray radiation dose received by the patient.

Various embodiments may improve the spatial resolution of the x-ray image in accordance with a factor, F, relative to the best spatial resolution that would otherwise be achievable in the image based on the size and/or spacing of the detector elements (i.e., pixels). As used herein, the spatial resolution of the image refers to the size of the smallest discernible feature of the image. Thus, in this context, "improving" the spatial resolution means that the spatial resolution is made smaller (i.e., such that smaller features are discernible in the image). By way of example, a detector having a pixel spacing, Sp may inherently result in a minimum achievable spatial resolution, R1, in the image without the use of an embodiment method. The various embodiments may improve (i.e., decrease) the achievable spatial resolution for the same detector in accordance with a factor, F, by providing an image having a second spatial resolution, R2, where R2=R1(1/F). In various embodiments, F>1.0, and may be between about 1.1 and about 10 (e.g., 1.2-5.0, such as 1.5-4.0), including between 1.5-2.0, 2.0-3.0, 3.0-4.0 and/or 4.0-5.0.

In one embodiment, for a detector having a pixel spacing Sp of about 1.0 mm or more (e.g., 1.0-2.0 mm), which would normally provide a spatial resolution of about 0.5 mm or greater in the image, the spatial resolution of the image obtained using the present invention may be improved to less than 0.5 mm (e.g., 0.1 mm to 0.45 mm, such as 0.2-0.4 mm, including about 0.25 mm).

The various embodiments may improve the resolution of the image using super-resolution. Super-resolution refers to a class of processing techniques for improving the resolution of an imaging system. In general, super-resolution techniques use information from several different images/frames to create an upsized image having improved resolution and lower noise (i.e., higher SNR). These techniques were originally developed in photography and video editing to improve the resolution beyond what would otherwise be possible based on the pixel size of the camera taking the images. Super-resolution techniques typically require that multiple images or frames be taken of the scene or object of interest from slightly different perspectives (e.g., the camera has moved slightly with respect to the object between images/frames). The techniques will not work if either the camera does not move at all relative to the object or the camera moves too much relative to the object between successive images/frames. In a typical super-resolution technique, an image/frame is upsized (i.e., the number of pixels is increased by some factor) and an interpolation algorithm is applied to generate an interpolated upsized image. Then, one or more regions within neighboring images/frames may be compared to estimate how much objects within the region(s) have moved between frames. Information from neighboring images/frames may then be intelligently merged with the interpolated upsized image to produce a super-resolution (SR) image which may have more information than is contained in any one of the originally-obtained images. In particular, the super-resolution image may have improved spatial resolution and/or SNR compared to the original image(s). The process may be repeated iteratively to further improve the spatial resolution and/or SNR.

In general, super-resolution techniques may involve attempting to reproduce or model the process by which image quality is lost using the camera/detector that obtained the lower-quality images and then solving the inverse problem of finding (e.g., reconstructing) the higher-quality image (e.g., an upsized image with improved spatial resolution and higher SNR) which would produce the known lower-quality images by that process. Various techniques and algorithms for improving spatial resolution and/or SNR of images using super-resolution are known.

Figure 6:
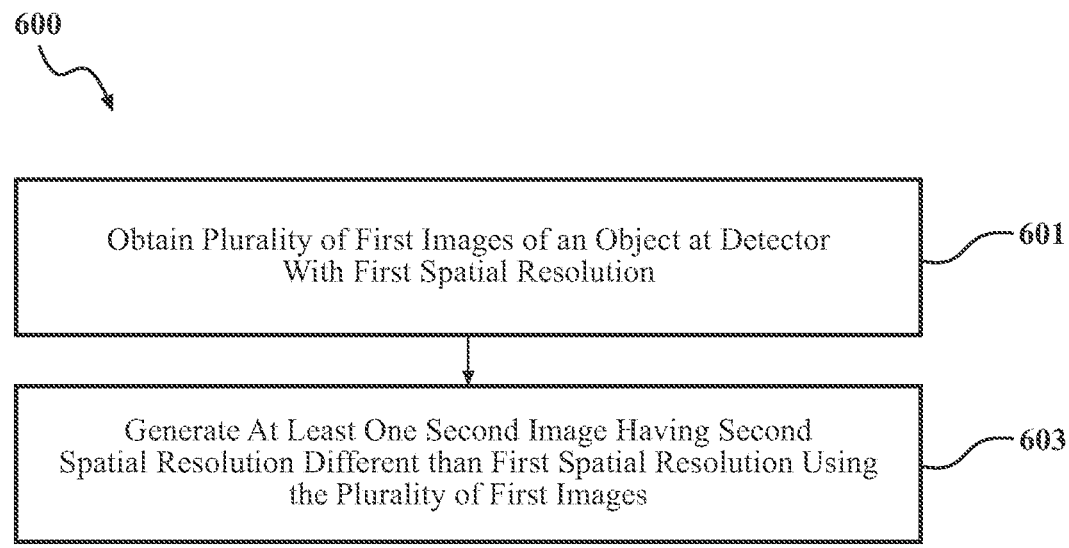
FIG. 6 is a process flow diagram illustrating a method for obtaining x-ray images with improved spatial resolution using super resolution.

FIG. 6 is a process flow diagram that illustrates a first embodiment method 600 for obtaining images using an imaging system that includes an x-ray source and an x-ray detector. The imaging system may be similar or identical to the systems shown in FIGS. 1-5C. The detector may be a "hybrid" CT/fluoroscopy detector such as shown in FIGS. 5A-5C where the x-ray beam is collimated to expose the second portion 503 of the detector area, as shown in FIG. 5C. Alternately, the detector may be a flat panel detector for fluoroscopy/cone beam imaging. The detector may have a size and shape that corresponds to the second portion 503 of the detector shown in FIGS. 5A-5C (i.e., with the elongated "wing" sections of the first portion 502 omitted), and may include, for example, a GOS scintillator, 2D anti-scatter plates, a curved detector surface, etc. Alternately, the detector may be a conventional flat panel detector with a flat, planar detector surface and may include, for example, a cesium iodide scintillator material. In some embodiments, the detector may be included in an external beam radiation treatment system, such as a linear accelerator (LINAC) system, as described in further detail below.

In block 601, a plurality of first x-ray images of an object (e.g., a human or animal patient) may be obtained at a detector with a first spatial resolution while the detector is moved slightly with respect to the source between images. The magnitude of the movement of the detector with respect to the source may be a sub-pixel length (i.e., less than the center-to-center spacing, Sp, between adjacent pixels).

In block 603, at least one second image of the object may be generated using the plurality of first x-ray images, where the at least one second image has a spatial resolution that is different than the first spatial resolution. The plurality of first images may be used to generate the at least one second image using a super-resolution technique as described above. In particular, information from the plurality of first images may be intelligently merged to produce a second super-resolution (SR) image which may have more information than is contained in any one of the original images. The SR image may be upsized (i.e., contain more pixels) than the original images(s) and have an improved spatial resolution as described above. The SR image may also have an improved SNR compared to the original image(s).

The at least one second image may be generated by a suitable computing device having a memory and a processor coupled to the memory, such as the computer 46 shown in FIG. 3. Alternately, the at least one second image may be generated using a memory and processor located on or within the detector. The processor may be configured with processor-executable instructions to receive electronic representations of the first images (i.e., frames of x-ray image data) obtained by the detector and to use the first images to generate a second image having improved spatial resolution and SNR, for example, using a super-resolution algorithm. In embodiments, as each first image is obtained and read out from the detector, the image (e.g., image frame) may be stored in a memory, and then combined with data from additional image(s) (i.e., preceding and/or subsequent frames from the detector) to generate a super-resolution image having an improved spatial resolution. For example, each second image may be generated by combining data from a certain number (e.g., 2-10, such as 3-5) of image frames from the detector. The data may be combined using a super-resolution technique, as described above.

In one exemplary embodiment, the detector may read out image frames at a rate that is greater than 30 Hz, such as at least about 60 Hz (e.g., 60-300 Hz), while the detector is moved a sub-pixel amount with respect to the x-ray source. The processor may combine a certain number of image frames (e.g., 5 frames) to generate a SR image. For example, if the detector system is reading out image frames at a first frame rate (e.g., 300 Hz), the processor may combine a set number of image frames (e.g., 5 frames) to produce SR images at a lower frame rate (e.g., 60 Hz). Alternately, the processor may generate SR images at the same frame rate as the image data is acquired by the detector by combining a set number of preceding frames with each new frame read out from the detector.

The generated SR images may be sent to a display device (e.g., workstation computer, monitor device, etc.) for real-time display of the SR images. In embodiments, the SR images may be transmitted via a wireless communication link from the gantry 40 to an external computing device. In some embodiments, a plurality of SR images may be generated from different projection angles as the rotor 41 rotates to different positions around the gantry 40. The plurality of SR images may be used as an input to a tomographic reconstruction algorithm (e.g., a backprojection algorithm), and to generate a tomographic reconstruction (e.g., cone-beam CT reconstruction) of the object using the SR images.

The imaging system may further include an apparatus for moving the detector relative to the x-ray source while the plurality of first images are obtained by the detector. For example, one or more actuators may be coupled to the detector system (e.g., to the detector chassis) to drive the motion of the detector relative to the x-ray source. FIG. 5C schematically illustrates an actuator device 507 that is configured to controllably displace the detector 501 by a sub-pixel amount. The actuator device 507 may comprise one or more piezoelectric motors, for example. The actuator device 507 may displace the detector 501 in at least one direction (i.e., in the x-axis direction 508 and/or the z-axis direction 509) and preferably in two orthogonal directions. The magnitude and direction of the displacement of the detector 501 between each image obtained by the detector may be known (e.g., via encoder feedback) or may be estimated or derived based on the operating conditions of the actuator device 507. Thus, complicated motion estimation processes that are typically used in super-resolution techniques may be greatly simplified or eliminated.

If the displacement of the detector relative to the source between multiple x-ray images is precisely known (e.g., via encoder data), then the generated SR images may exhibit a 4-5 times improvement in spatial resolution relative to the originally-obtained images. However, even where the displacement is not known, a motion estimation algorithm may be used to improve the spatial resolution by at least about a factor of two.

Super-resolution techniques may be used to improve spatial resolution and also to increase SNR of the originally obtained image. Thus, in embodiments, the plurality of first images may be obtained using a relatively lower output power (i.e., lower x-ray dosing) from the x-ray source 43. This may decrease the SNR of the first images obtained at the detector. However, the SNR may be restored in the at least one second image generated from the plurality of lower SNR first images using a super-resolution technique as described above. In some embodiments, the SNR of the first plurality of images may be below generally acceptable levels for use in diagnostic imaging. However, the SNR of the generated second image(s) may be sufficiently high for use in diagnostic imaging.

Further embodiments include methods and systems for performing cone beam CT imaging using scan paths that follow non-planar trajectories. In a typical cone beam CT scan, the x-ray source and detector rotate around the patient in a single scan plane along a circular trajectory. A plurality of 2D x-ray projections are obtained by the detector from different projection angles as the source and detector rotate, and are used to generate a 3D reconstruction of a region of interest. In the tomographic reconstruction, the highest image quality is found in the central (axial) slice of the reconstruction, with image quality decreasing as a function of distance from the central slice. This is because the central slice, which corresponds to the scan plane of the x-ray source, has the most complete set of projection data from every projection angle, while there is less projection data for the slices further away from the central slice. This may result in artifacts in the reconstructed image, particularly in the peripheral slices.

In various embodiments, a cone beam CT imaging system that uses non-planar scan trajectories, such as a sinusoidal trajectory, may be utilized to obtain more complete set of projection data for reconstruction of slices outside of the central slice. The resulting 3D reconstruction may be characterized by improved image quality and reduced artifacts. The imaging system may be similar or identical to any of the systems shown in FIGS. 1-5C. The detector may be a panel detector having a length dimension of at least about 20 cm (e.g., 30-40 cm) and a width dimension of at least about 20 cm (e.g., 30-40 cm). The detector may be a "hybrid" CT/fluoroscopy detector such as shown in FIGS. 5A-5C where the x-ray beam is collimated to expose the second portion 503 of the detector area. In some embodiments, the imaging system may be integrated in an external beam radiation treatment system, such as a linear accelerator (LINAC) system, as described in further detail below.

Figure 7A:
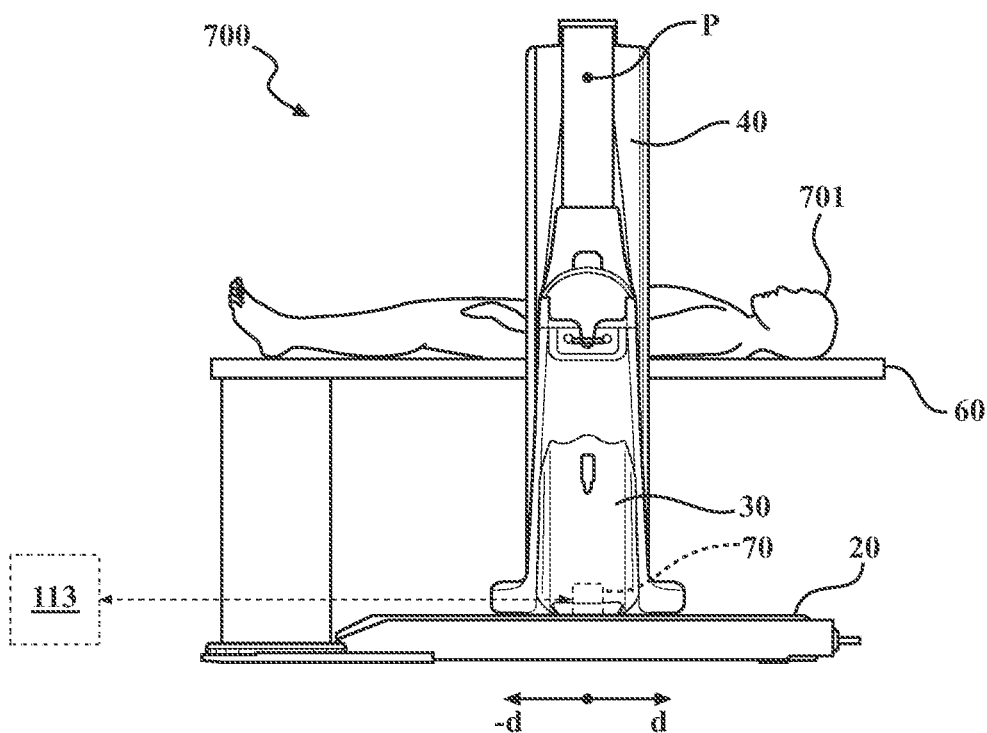
FIGS. 7A-7G schematically illustrate a method of performing cone beam CT imaging using a sinusoidal circular trajectory.
Figure 7B:
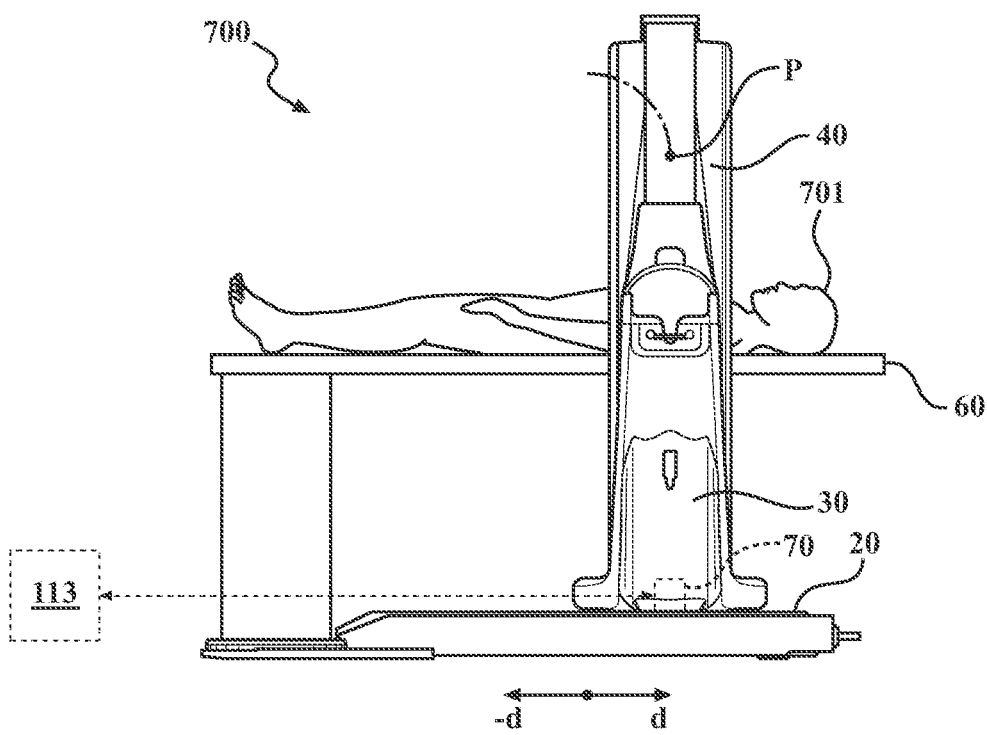
Figure 7C:
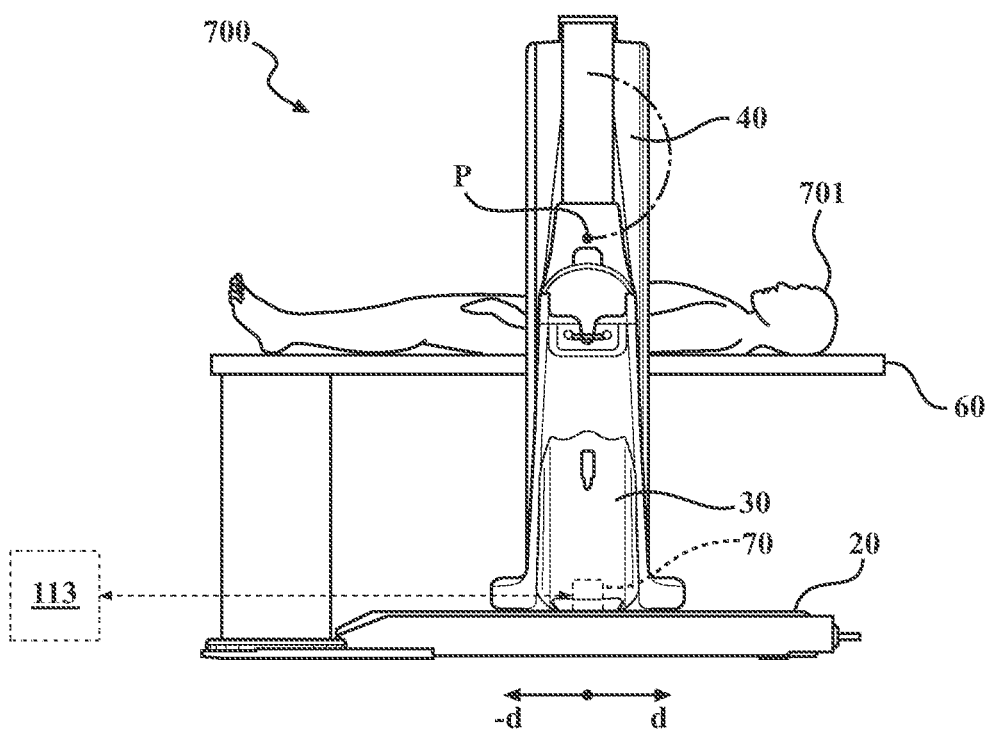
Figure 7D:
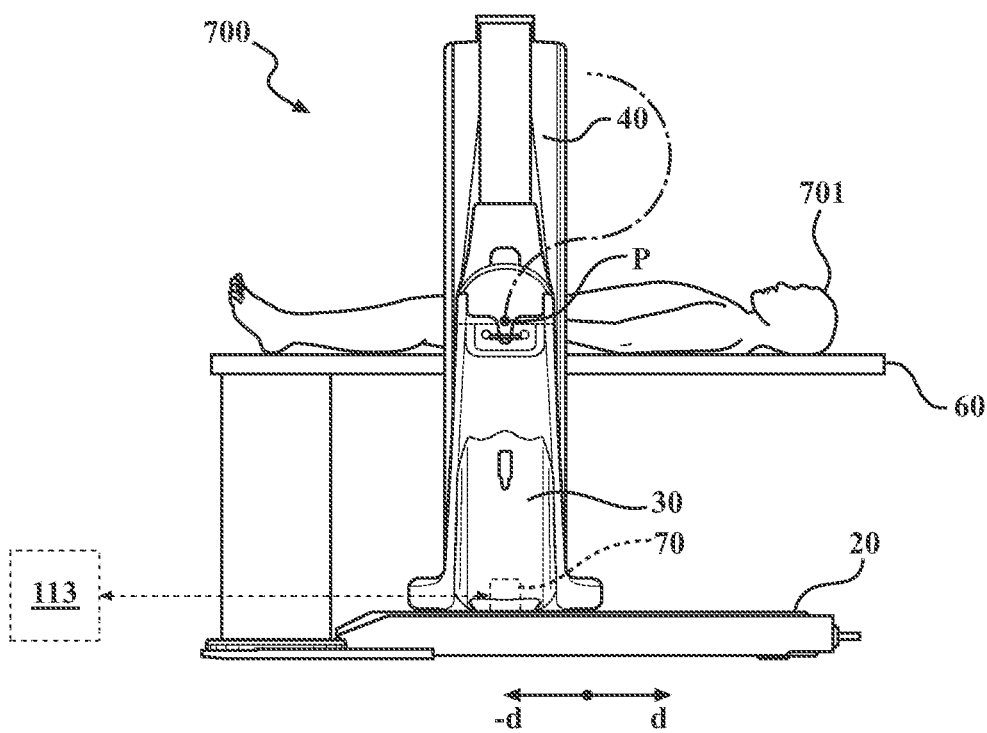
Figure 7E:
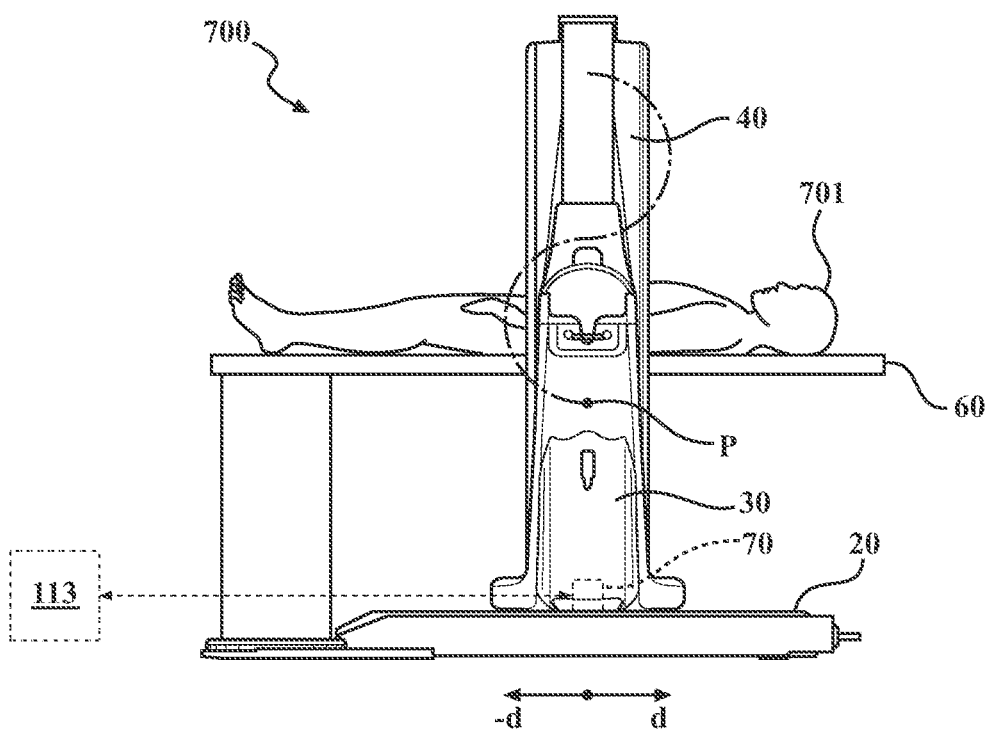
Figure 7F:
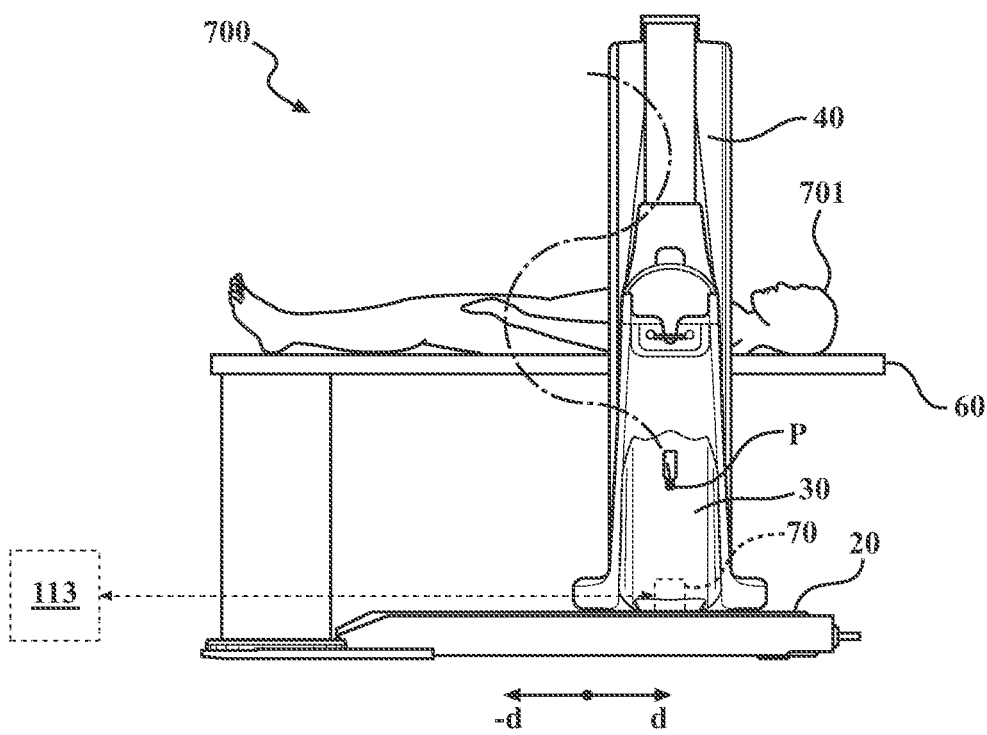
Figure 7G:
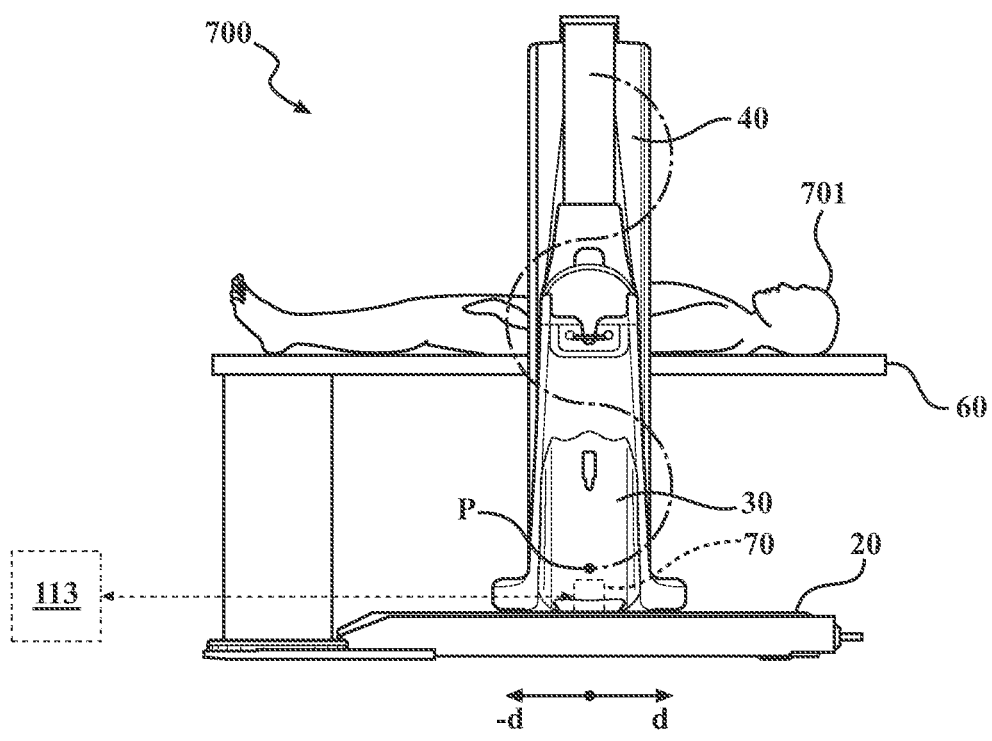

FIGS. 7A-7G schematically illustrate a method of performing cone beam CT imaging of an object (e.g., a human or animal patient) using a sinusoidal circular trajectory. The imaging system 700 in this embodiment is similar to the imaging system shown in FIG. 1, and includes, for example, a base 20, a patient support 60 supported above the base, and an imaging gantry 40 supported by a gimbal 30, where a drive mechanism 70 drives the translation of the gantry 40 and gimbal 30 along the length of the base 20. The system controller 113 may control the imaging system 700 to perform a coordinated translation of the gantry 40 as the x-ray source rotates around the patient 701 (e.g., via a rotor 41 within the gantry 40 as shown in FIG. 3) so that the focal spot of the x-ray source follows a sinusoidal-shaped trajectory as it rotates around the patient 701. This is schematically illustrated in FIGS. 7A-7G, which shows the focal spot of the x-ray source (indicated by point, P) rotating 180° from the top of the gantry 40 (FIG. 7A) to the bottom of the gantry (FIG. 7G). As the source rotates, the system controller 113 controls the drive system 70 to translate the gantry 40 back and forth along the z-axis so that the focal spot, P, follows a sinusoidal path around the patient 701, as indicated by the dashed line in FIGS. 7B-7G. As the gantry 40 continues to rotate around the patient 701, the gantry may continue to translate along the z-axis. In the embodiment of FIGS. 7A-7G, for each 360° rotation of the source around the patient, the trajectory of the x-ray focal spot, P, may trace out three "peaks" and three "valleys" in the z-axis direction, or a sinusoid of order m=3. In other embodiments, the sinusoid may be of order m=2, m=4, m=5, etc.

The displacement of the gantry 40 (i.e., ±d shown in FIGS. 7A-7G) may be less than the width of the detector in the z-direction. In embodiments, the gantry 40 may be displaced by a fraction of the detector width, such as ½, ⅓, ¼, ⅙, ⅛, etc. of the detector width. The positions of the gantry 40 along the z-axis during the scan may be provided to the CT reconstructor (e.g., via encoder data) and combined with the projection data and rotor encoder data to perform tomographic reconstruction.

An imaging system such as shown in FIG. 2 may also be used to perform cone beam CT imaging using a sinusoidal circular trajectory. For example, for a patient supported in a horizontal configuration, drive mechanism 208 may be controlled to translate the gantry 40 and support column 201 back-and-forth in a horizontal direction in coordination with the rotation of the x-ray source so that the source follows a sinusoidal trajectory relative to the patient. For a patient supported in a vertical, weight-bearing configuration, drive mechanism 203 may be controlled to translate the gantry 40 up-and-down on the support column 201 to provide a sinusoidal scan trajectory. When the patient is supported in a tilted configuration, drive mechanisms 203 and 208 may be controlled to move the gantry 40 up and down along the tilted axis to provide a sinusoidal scan trajectory.

In a sinusoidal circular trajectory as shown in FIGS. 7A-7G, the x-ray source rotates around the patient while the gantry translates along the patient axis to provide a sinusoidal scan trajectory over the surface of an imaginary cylinder. In further embodiments, the x-ray source may rotate around the patient in coordination with a rotation of the gantry about its isocenter to provide a sinusoidal spherical trajectory. In a spherical circular trajectory, the sinusoidal-shaped path of the x-ray focal spot extends over the surface of an imaginary sphere centered on the isocenter of the gantry.

Figure 8A:
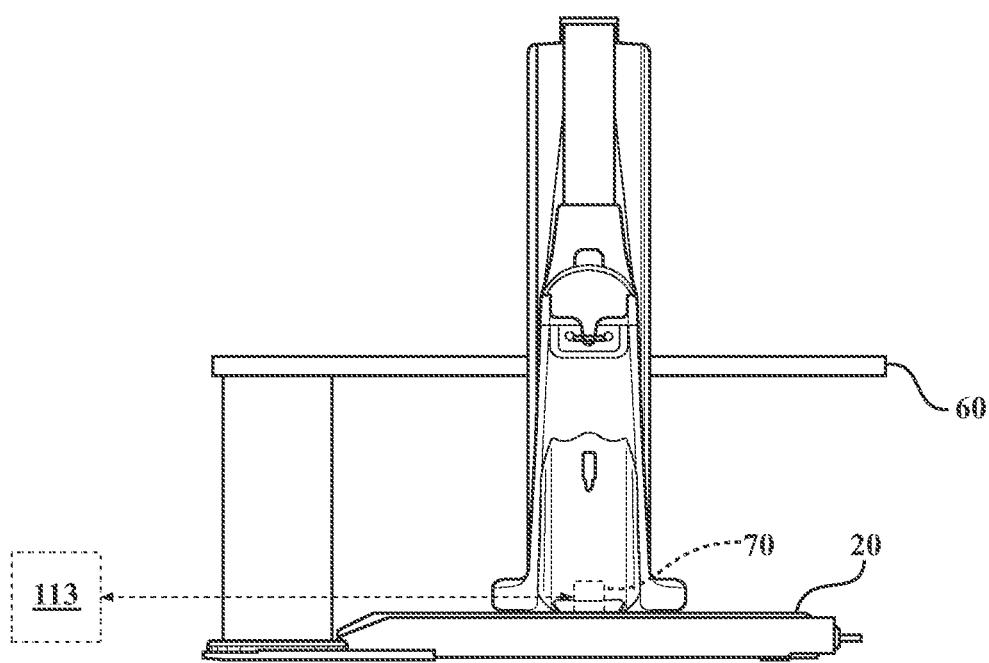
FIGS. 8A-8B schematically illustrate an x-ray imaging gantry rotated about a vertical axis for performing cone beam CT imaging using a sinusoidal spherical trajectory.
Figure 8B:
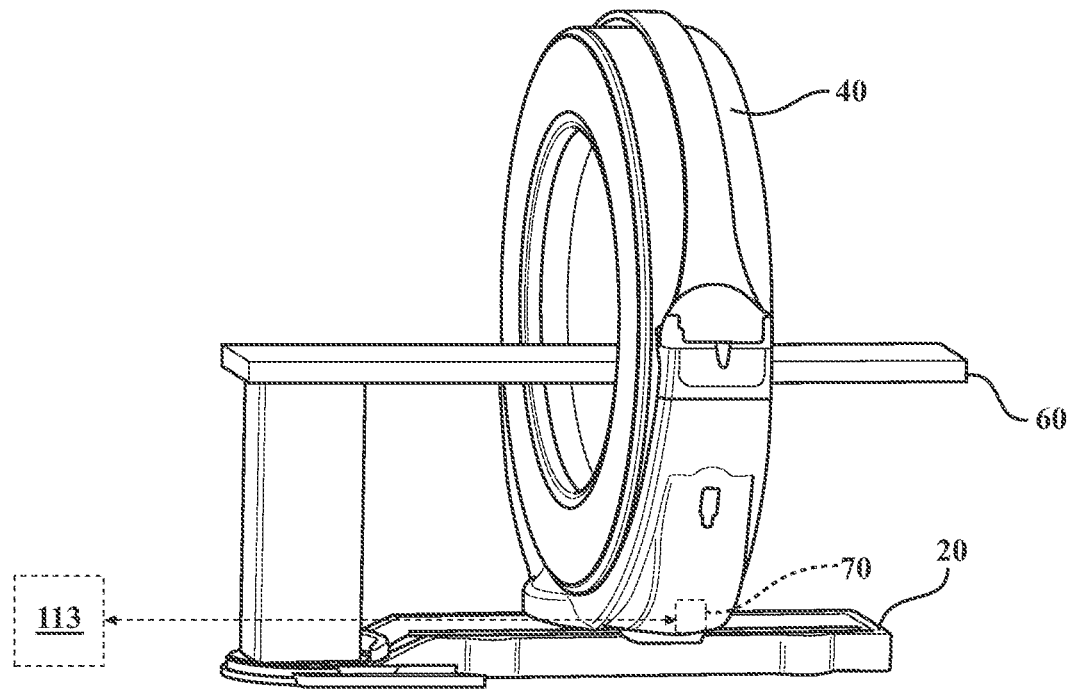

In the imaging system of FIG. 1, for example, the system controller 113 may control the motorized system 112 to perform a coordinated rotation of the gantry 40 about axis 102 (i.e., "wag" rotation) as the x-ray source rotates around the patient 701 so that the focal spot of the x-ray source follows a sinusoidal spherical trajectory. This is schematically illustrated in FIGS. 8A and 8B, which illustrates the "wag" rotation of the gantry 40. Alternately or in addition, the system controller 113 may control the motorized system 115 (see FIG. 1) to perform a coordinated rotation of the gantry 40 about axis 107 (i.e., "tilt" rotation) to provide a sinusoidal spherical scan trajectory.

Similarly, in the imaging system of FIG. 2, the system controller 213 may control drive mechanisms 212 and 208 to rotate the gantry 40 about pivot axis 211 while translating the gantry 40 in the direction opposite to the direction of rotation to provide isocentric "wag" rotation while the x-ray source rotates to provide a sinusoidal spherical scan trajectory. Alternately or in addition, the system controller 213 may control drive mechanism 205 to perform a coordinated rotation of the gantry 40 about axis 207 with the rotation of the x-ray source to provide a sinusoidal spherical scan trajectory.

Figure 9:
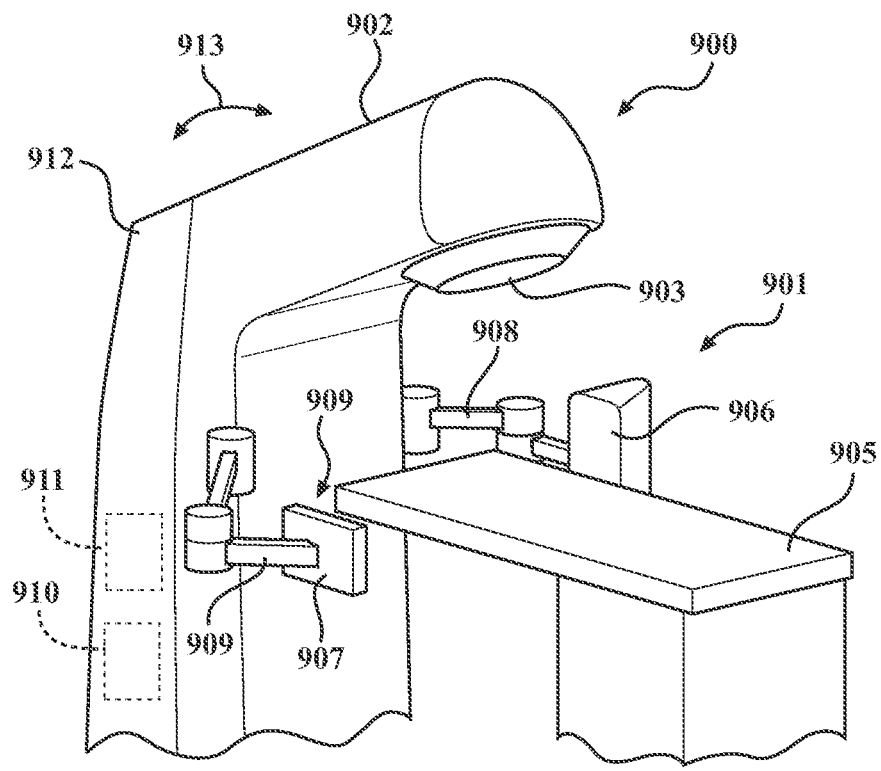
FIG. 9 illustrates an external beam radiation treatment system that includes an integrated x-ray imaging system.

FIG. 9 illustrates an external beam radiation treatment system 900, such as a linear accelerator (LINAC) system, a gamma knife system or a proton beam radiosurgery system, that includes an integrated x-ray imaging system 901, in accordance with various embodiments. FIG. 9 illustrates a LINAC system that includes a rotating gantry 902 and a patient support 905 (e.g., couch) on which a patient may be supported. The gantry 902 may rotate relative to a support structure 912 in the direction of arrow 913. The gantry 902 includes a head 903 that emits a high-energy (e.g., MeV-range) beam of radiation that may be directed to a target location (e.g., a tumor) within the patient's body. The head 903 may be rotated around the patient to irradiate the patient from any angle. The patient support 905 may be moveable to adjust the position and/or orientation of the patient relative to the head 903.

In a typical external beam radiation treatment, one or more pre-operative images (e.g., CT scan and/or MRI images) of the patient may be used for pre-treatment planning. The pre-treatment planning may include identifying the location of the target tissue (e.g., tumor(s)) to be irradiated, as well as identifying the location of other tissue (e.g., "organs at risk") to be avoided. At the time of treatment, an imaging device located in the treatment suite may be used to obtain additional images of the patient, such as 2D x-ray fluoroscopic images and/or a 3D x-ray cone beam CT image. The additional image(s) may be matched to the pre-operative images to enable the patient to be positioned in the same coordinate system (relative to the LINAC head 903) as was used for the pre-operative planning. In the embodiment shown in FIG. 9, the imaging device 901 may be integrated with the treatment system 900, and may include an x-ray source 906 and a detector 907 mounted opposite one another on the rotating gantry 902. The source 906 and detector 907 may each be offset from the head 903 by 90° and may rotate together with the head 903 on the gantry 902. The source 906 and detector 907 may be mounted to the gantry 902 by a pair of arms 908, 909 (e.g., robotic arms) that may enable a limited amount of controlled movement of the source 906 and detector 907 relative to the gantry 902 and head 903.

External beam radiation treatment systems that include integrated x-ray imaging equipment commonly use flat panel detectors. The image quality obtainable from such detectors is generally not sufficient for use directly for pre-treatment planning purposes. The images from such detectors are typically used to match bony landmarks visible in the images to the same landmarks in pre-operative images used in pre-treatment planning, which are generally of much higher image quality and may enable clearer visualization of tumors and other soft tissue of the patient. A patient may receive external beam radiation treatment therapy over the course of multiple (e.g., daily) treatment sessions that can last several weeks. During the course of the therapy sessions, the target tissue (e.g., tumor) can shrink significantly and can also move within the patient's body. However, changes in the size, shape and/or location of the target tissue may not be evident from the images (e.g., 2D fluoroscopy and/or cone beam CT images) obtained using the x-ray imaging equipment located at the point-of-treatment.

Various embodiments of an external beam radiation treatment system 900 having an integrated x-ray imaging system 901 utilize a detector 907 that provides improved image quality relative to a conventional flat panel detector. In embodiments, the detector 907 may be similar to the detectors described above with reference to FIGS. 4A-4G and 5A-5C. For example, the detector 907 may include a curved profile in which the detector elements or modules are arranged along an arc centered on the focal spot of the x-ray source 906. The detector 907 may have a curved profile along the length dimension and/or along the width dimension. The detector 907 may be a modular detector such as described with reference to FIGS. 4A-4G. Each module may include a scintillator (e.g., GOS), a photodiode array, and an electronics assembly including analog-to-digital (A/D) converter circuitry for converting the output signals from the photodiode array to digital signals. A plurality of modules may be mounted to a chassis in abutting fashion to form a detector panel having a desired size, shape and cross-sectional profile. The detector 907 may utilize a double- or multiple-buffering configuration and may enable continuous exposure, as described above. The detector 907 may also include a 1D or 2D anti-scatter assembly, as is also described above. The detector 907 according to various embodiments may provide diagnostic-quality images at the treatment site that may be used for pre-treatment planning or modification to an existing treatment plan for external beam radiation therapy of a patient.

The imaging system 901 may also be used to generate images having improved spatial resolution and/or SNR using a super-resolution (SR) technique, as described above. In particular, a plurality of first x-ray images of the patient may be obtained using the detector 907 while the detector 907 is moved slightly with respect to the source 906 between images. The magnitude of the detector movement 907 may be in the sub-pixel range (i.e., less than the center-to-center spacing, Sp, between adjacent pixels). The first images may be fed to a computer 910 that may use the first image to generate at least one second image using a super-resolution technique as described above. The generated second image may be upsized (i.e., contain more pixels) than the first images and may have an improved spatial resolution compared to the first images. The second image may also have an improved SNR compared to the first images.

The movement of the detector 907 relative to the source 906 between successive x-ray images may be achieved by moving the arm 909 to which the detector 907 is mounted. The system 900 may include a controller 911 (e.g., a computer) that may be configured to send control signals the arms 908, 909 to control the movements of the arms 908, 909. The controller 911 may control the arm 909 to move the detector 907 by a sub-pixel amount between the acquisition of each of the first images that are used to generate the super-resolution images. Alternately or in addition, a separate actuator system (e.g., one or more piezoelectric motors) may be operatively coupled to the detector 907 to drive the motion of the detector 907 relative to the x-ray source 906, as described above.

In various embodiments of a system 900 as shown in FIG. 9, the gantry 902 may be rotated to obtain 2D x-ray images of the patient from desired projection angles. Alternately or in addition, the gantry 902 may rotate around the patient while the x-ray source 906 and detector 907 obtain a set of projection data that may be used to generate a 3D cone-beam CT reconstruction. The detector 907 size may provide a limit on the field-of-view of the images that may be obtained. For example, a detector 907 with a dimension of 30-40 cm may only provide a reconstruction volume of ~15-20 cm diameter in the axial plane of the patient.

Figure 10:
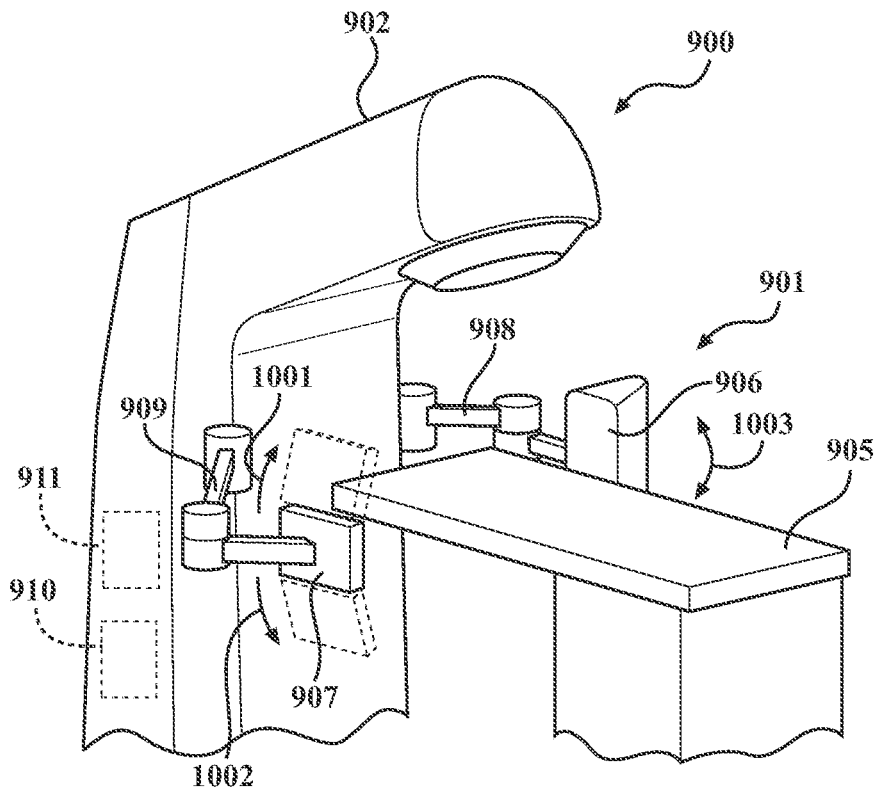
FIG. 10 schematically illustrates an external beam radiation treatment system with an integrated x-ray imaging system having a detector that is moveable with respect to the focal spot of the x-ray source to increase the field-of-view of the imaging system.

Various embodiments include controlling the arm 909 to move the detector 907 along an arc or line with respect to the focal spot of the x-ray source to effectively increase the field-of-view of the detector 907. This is schematically illustrated in FIG. 10, which shows the detector 907 (in phantom) moved to different positions along the directions of arrows 1001, 1002. The controller 911 may control the arm 909 to move the detector 907 by a desired distance (e.g., a fraction of a panel length, such as ½ a panel length, a full panel length or more) from an initial position. The system 900 may obtain multiple images from the same projection angle with the detector translated to different positions with respect to the x-ray focal spot. The multiple images may be combined in software (e.g., using computer 910) to generate images having a larger effective field-of-view. To perform an imaging scan, the gantry 902 may rotate the source 906 and detector 907 around the patient to obtain a first set of projection data with the detector 907 at a first position relative to the x-ray focal spot, the arm 909 may move the detector 907 to a second position relative to the focal spot, and the gantry 902 may rotate the source 906 and detector 907 around the patient again to obtain a second set of projection data with the detector 907 located in the second position. The process may optionally be repeated with the detector 907 moved to additional positions relative to the x-ray focal spot. In one example, the gantry 902 may perform a full 360° rotation around the patient to obtain a first set of projection data at a plurality of rotational positions, the detector 907 may then be moved (e.g., via a half- or full-panel length) and the gantry 902 may perform another 360° rotation (e.g., a counter-rotation) to obtain a second set of projection data at the same rotational positions. Alternately, the gantry 902 may perform a partial rotation (e.g., a 180° rotation) with the detector 907 in a first position, the detector 907 may be moved to a second position, and the gantry 902 may continue the rotation (e.g., another 180°).

In other embodiments, an imaging scan may be performed by rotating the gantry 902 to a plurality of rotation angles around the patient, and at each rotation angle, moving the detector 907 to different position(s) relative to the focal spot and obtaining multiple sets x-ray image data with the detector 907 moved to each position.

In embodiments, the x-ray source 906 may include a mechanism that alters a characteristic of the output x-ray beam based on the position of the detector 907. In one embodiment, the x-ray source 906 may include an adjustable collimator that may shape the beam output such that the detector 907 remains exposed to x-rays at it moves to different positions, while portion(s) of the beam not incident on the detector 907 are blocked. Alternately or in addition, the arm 908 may be controlled to pivot the x-ray source 906 about the stationary focal spot (indicated by arrow 1003 in FIG. 10) in coordination with the movement of the detector 907 so that the x-ray beam remains centered on detector 907. This may minimize the patient's exposure to x-rays in regions outside of the field-of-view of the detector and enable safer and more efficient dose utilization.

Figure 11:
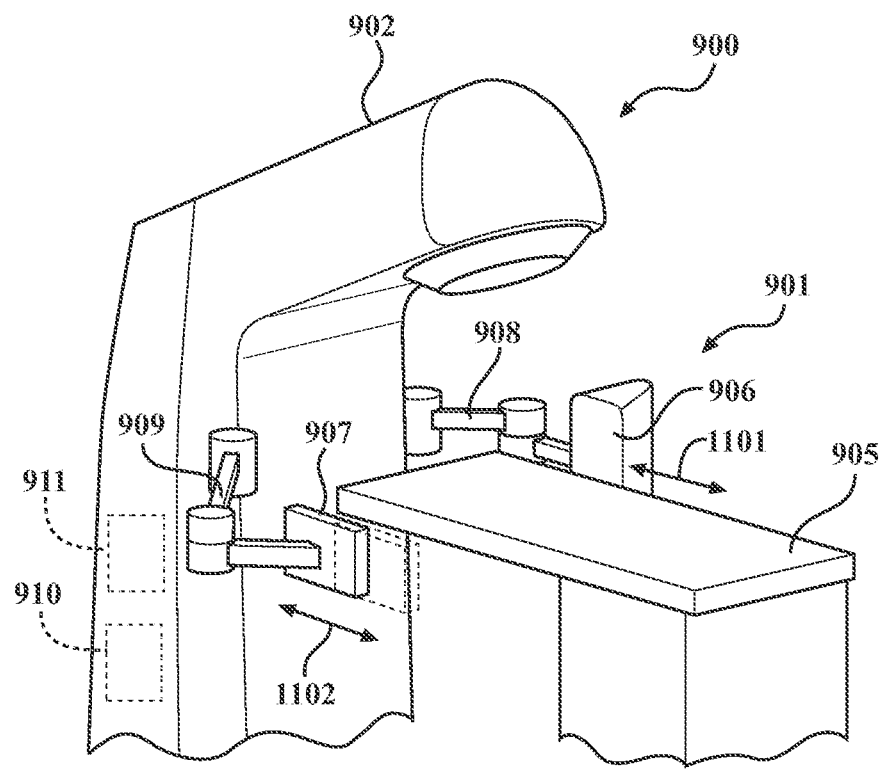
FIG. 11 schematically illustrates an external beam radiation treatment system with an integrated x-ray imaging system that performs cone beam CT imaging using a sinusoidal scan trajectory.

In further embodiments, the system 900 may utilize non-planar scan trajectories, such as a sinusoidal trajectory, to obtain a more complete set of projection data for cone-beam CT imaging. In one example, the controller 911 may control the arms 908, 909 to translate the source 906 and detector 907 back and forth along the length of the patient in the direction of arrows 1101, 1102, as shown in FIG. 11. The translation of the source 906 and detector 907 may be coordinated with the rotation of the gantry 902 so that the focal spot of the x-ray source follows a sinusoidal circular trajectory as it rotates around the patient. Alternately, the arms 908, 908 may be controlled to move the source 906 and detector 907 over an imaginary spherical surface to provide a sinusoidal spherical trajectory, as described above.

In embodiments, the controller 911 may control the arms 908, 909 to move the source 906 and detector 907 in a sinusoidal scan trajectory while arm 909 may move the detector 907 along an arc or line with respect to the focal spot of the x-ray source 906 to effectively increase the field-of-view of the detector 907. For example, the source 906 and detector 907 may move back and forth in the z-axis direction as shown in FIG. 11 to provide a sinusoidal circular scan trajectory and the detector 907 may also be moved in the transverse direction with respect to the focal spot of the source 906 to extend the effective field-of-view, as illustrated in FIG. 10. For example, the gantry 902 may perform a full (i.e., 360°) or partial (e.g., 180°) rotation with the source 906 and detector 907 moving in a sinusoidal trajectory and the detector 907 in a first position with respect to the x-ray focal spot. The detector 907 may then be moved to a second position with respect to the focal spot, and the gantry 902 may perform another rotation or continue the current rotation around the patient with the source 906 and detector 907 moving in a sinusoidal trajectory.

Translating the source 906 and/or detector 907 on the arms 908, 909 as schematically shown in FIG. 11 may enable the field-of-view of the imaging system 901 to be effectively increased in the z-axis dimension (i.e., along the patient length). This may enable the system to follow a contrast agent injected into the patient as it progresses through the patient's body, for example. The translation of the source 906 and detector 907 may also enable the imaging system 901 to perform helical cone-beam CT scans along the length of the patient.

In a typical helical CT scan, the source and detector are rotated continuously around the patient while either the patient is moved within the imaging bore or the imaging gantry is moved over the patient so that the x-ray source defines a helical or spiral trajectory around the patient. However, many rotating-gantry external beam radiation systems (e.g., LINAC systems) can rotate and counter-rotate over a limited range but do not enable continuous rotation of the gantry. This may limit the field-of-view of the CT reconstruction along the length of the patient.

Figure 12:
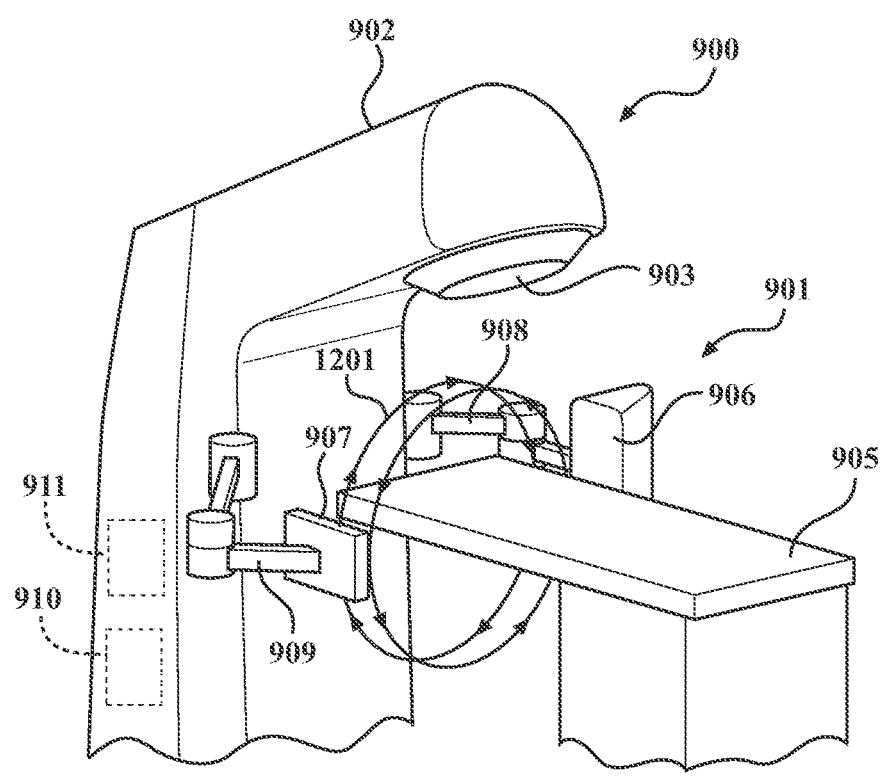
FIG. 12 schematically illustrates an external beam radiation treatment system with an integrated x-ray imaging system that performs cone beam CT imaging using a reverse helical trajectory.

Further embodiments include operating an external beam radiation system 900 having an integrated imaging system 901 to perform a reverse helical scan of a patient. In embodiments, the controller 911 may control the arms 908, 909 to translate the source 906 and the detector 907 in a first translation direction along the length of the patient as the rotor rotates the source 906 and detector 907 in a first rotational direction (i.e., clockwise or counter-clockwise) around the patient. The gantry 902 may perform a full (i.e., 360°) or partial (e.g., 180°, 270°, etc.) rotation around the patient. The gantry 902 may then counter-rotate in a second rotational direction opposite the first rotational direction while the arms 908, 909 may continue to translate in the first translation direction. The gantry 902 may continue to alternate its rotational direction while the arms 908, 909 continue to translate the source 906 and detector 907 in the first direction along the patient length to provide a reverse helical scan trajectory. This is schematically illustrated by FIG. 12, which shows the trajectory (indicated by arrow 1201) of the detector 907 around and along the length of the patient. In embodiments, the source 906 and detector 907 may translate at least about 0.5 meters along the length of the patient during a reverse helical scan. This may enable the CT reconstruction to have a larger field-of-view along the patient length, which may encompass, for example, complex tumors that extend down the length of the patient's spine.

In some embodiments, the system 900 may perform a scan along a reverse helical trajectory while arm 909 may move the detector 907 along an arc or line with respect to the focal spot of the x-ray source 906 to effectively increase the field-of-view of the detector 907. For example, the source 906 and detector 907 may translate in a first direction while the gantry rotates and counter-rotates as described above while the detector 907 is in a first position relative to the focal spot of the detector 907. The arm 909 may then move the detector 907 to a second position relative to the source 906 (e.g., by translating the detector 907 by one-half panel width), and the system 900 may perform another reverse helical scan in the reverse direction by translating the source 906 and detector 907 in a second direction back down the length of the patient while the gantry rotates and counter-rotates.

In some embodiments, the detector 907 may have an integrated processor unit that may be configured to perform all or a portion of the image processing operations, including tomographic reconstruction. The integrated processor unit may be an alternative or in addition to the separate computer 910 shown in FIGS. 9-12. The integrated processor unit may receive inputs of encoder position(s) (e.g., indicating the rotation position of the gantry 902 and/or the configurations of the arms 908, 909), source-to-detector distance, x-ray photon flux and/or x-ray source temperature (e.g., from a reference detector as described in U.S. Pat. No. 9,111,379). The integrated processor unit may be configured to perform various image correction techniques on the image data, such as offset correction, gain correction and/or pixel correction. In some embodiments, the integrated processor unit may also perform other real-time processing operations (e.g., for 2D fluoroscopy), including edge enhancement, recursive noise reduction and super resolution techniques. The processed images may be transmitted from the detector 907 to another entity, such as to a separate workstation.

Although the external beam radiation treatment system 900 shown in FIGS. 9-12 includes a pair of arms 908 and 909 extending from opposite sides of the gantry 902, it will be understood that other configurations are possible. For example, a single arm (e.g., 908 or 909) may extend from the gantry 902 and support both the source 906 and detector 907. A second arm may extend in a transverse direction (e.g., beneath the patient table 905 in FIG. 9) to couple the source 906 and detector 907 and maintain a constant spacing between the source 906 and detector 907.

Figure 13:
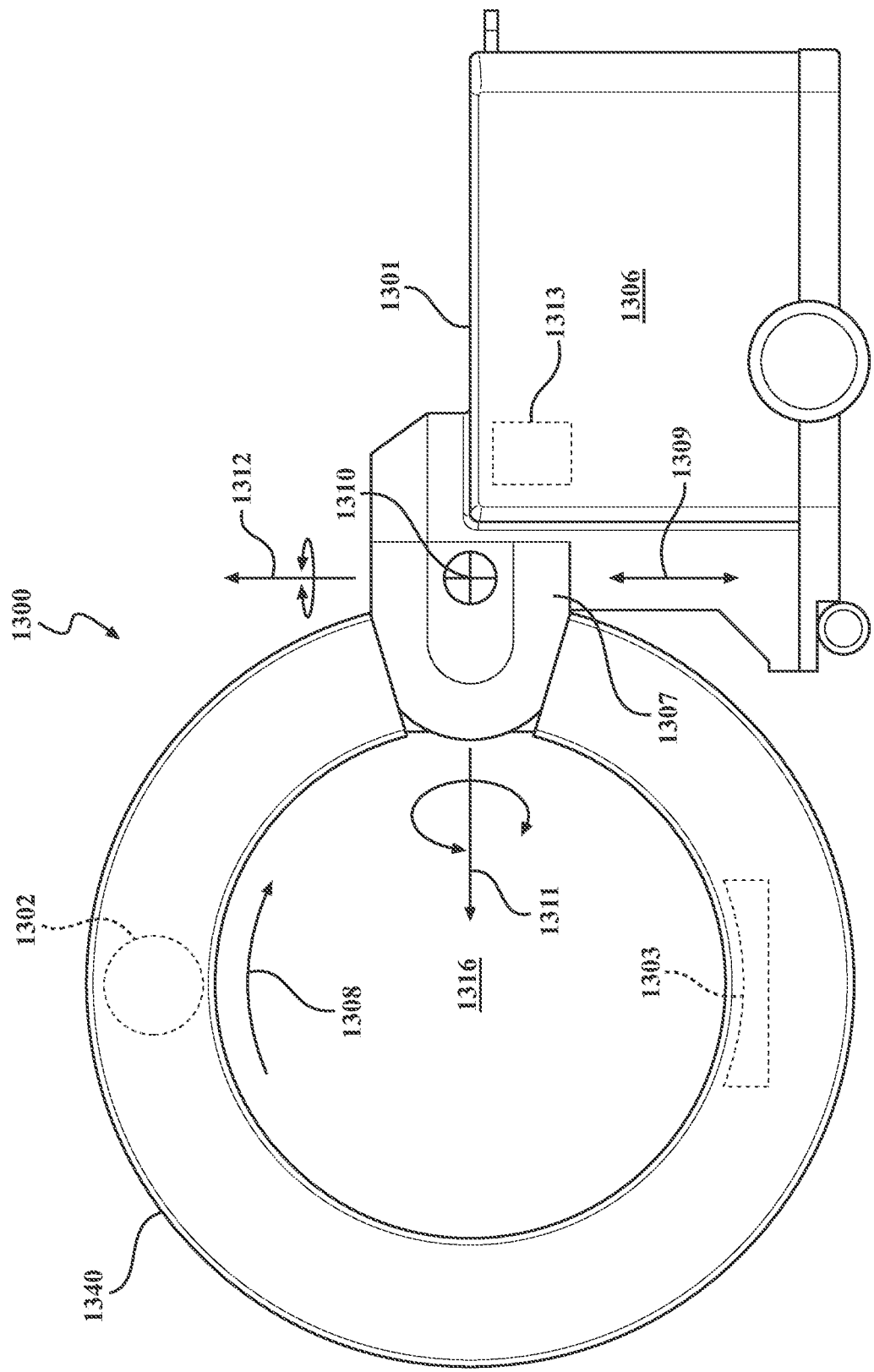
FIG. 13 illustrates a mobile x-ray imaging device that may be used to perform various embodiment methods.

FIG. 13 illustrates yet another embodiment of an imaging system 1300. In this embodiment, the imaging system 1300 includes an O-shaped imaging gantry 1340 that is mounted to a support structure 1301 in a cantilevered fashion. The imaging system 1300 may be an x-ray imaging system that may be used to obtain 2D fluoroscopic images and/or 3D tomographic images of an object located within the bore 1316 of the gantry. At least one of an x-ray source 1302 and an x-ray detector 1303 may rotate around the interior of the gantry (as shown by arrow 1308) to obtain images of an object within the bore 1316 from different projection angles. The support structure 1301 may comprise a mobile cart 1306 that is attached to one side of the gantry via an attachment mechanism 1307. The attachment mechanism 1307 may include one or more motorized systems that enable the gantry 1340 to translate and/or rotate with respect to at least a portion of the cart 1306. For example, in embodiments the gantry 1340 may be raised or lowered relative to the cart 1306 in the direction of arrow 1309. The gantry 1340 may also translate relative to the cart 1306 over a limited range (e.g., 30-50 cm, such as about 40 cm) in the direction of the z-axis 1310 (i.e., into and out of the page in FIG. 13). In addition, in some embodiments the gantry 1340 may be rotated with respect to the cart 1306 along at least one rotational axis. For example, the gantry 1340 may be tilted with respect to the cart 1306 about a horizontal axis 1311. The gantry 1340 may also be pivoted with respect to the cart 1306 about a vertical axis 1312. The gantry 1340 may perform an isocentric "wag" rotation via a combination of pivot of the gantry 1340 about the vertical axis 1312 and a translation of the gantry 1340 along the z-axis 1310 with respect to the cart 1306. A control system 1313 (e.g., a computer) may control the operation of the imaging system 1300, including the translational and rotational movements of the gantry 1340 relative to the cart 1306.

In some embodiments, the detector 1303 in the system 1300 shown in FIG. 13 may be a conventional flat-panel detector. Alternately, the detector may be a diagnostic quality CT detector similar to the detectors described above with reference to FIGS. 4A-4G, 5A-5C and 9-12. For example, the detector 1303 may include a curved profile and/or an anti-scatter assembly located over the detector elements. The detector 1303 may utilize a high-speed scintillator (e.g., GOS) and associated electronics, and may enable continuous exposure with a high readout rate. In some embodiments, the detector 1303 may be configured to provide improved spatial resolution and/or SNR using super resolution techniques, as described above.

In embodiments, the control system 1313 may control the imaging system 1300 to translate and/or rotate the gantry 1340 in coordination with the rotation of the source 1302 and detector 1303 to perform an imaging scan using a sinusoidal scan trajectory, such as a sinusoidal circular trajectory or a sinusoidal spherical trajectory, as discussed above. In some embodiments, the control system 1313 may control the imaging system 1300 to translate the gantry 1340 along the z-axis in coordination with a rotation and counter-rotation of the source 1302 and detector 1303 within the gantry 1340 to perform a cone-beam CT scan using a reverse helix trajectory. In some embodiments, the detector 1303 may include a mechanism that moves the detector 1303 by a sub-pixel amount to enable super-resolution imaging as described above.

Figure 14:
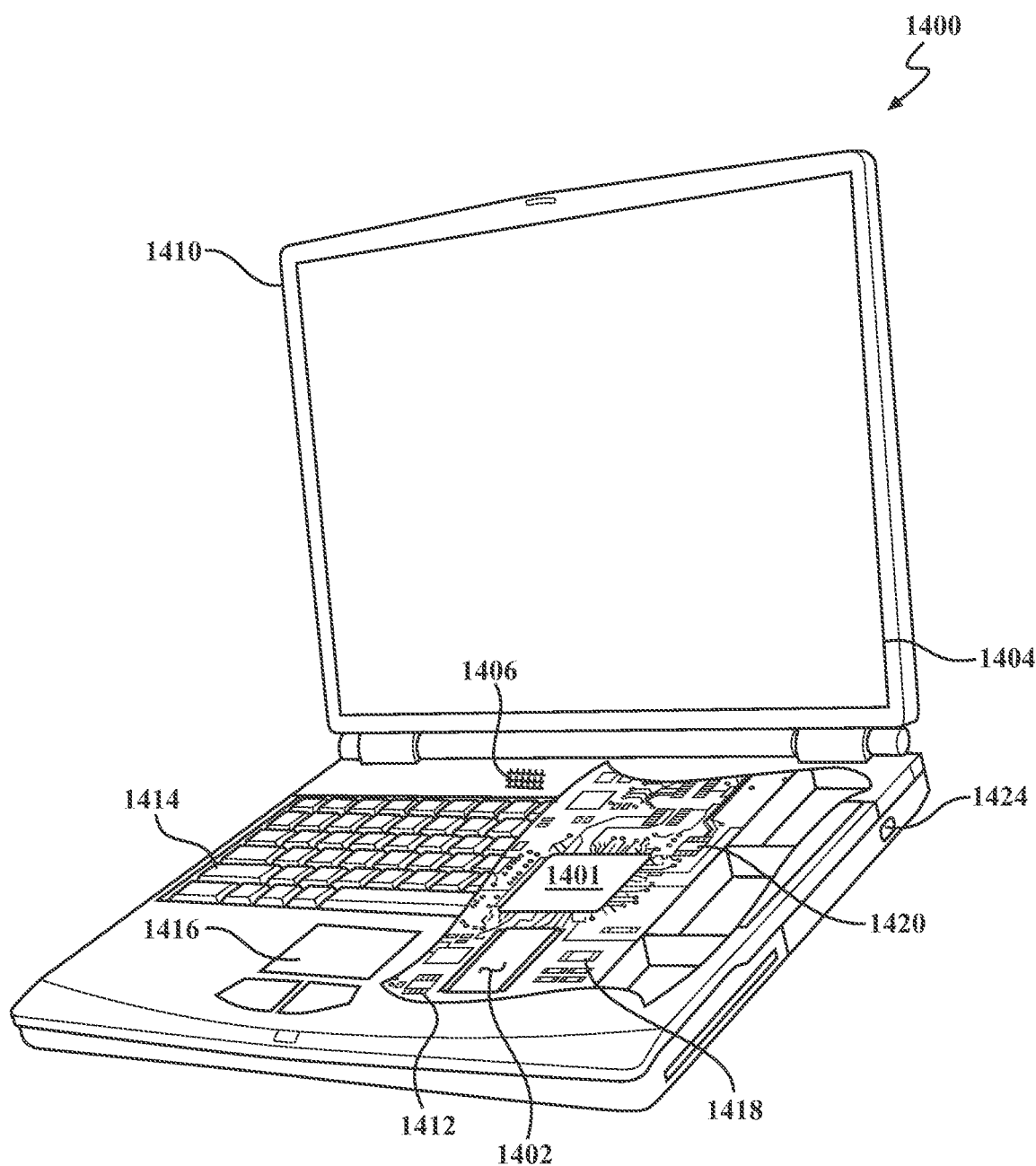
FIG. 14 schematically illustrates a computing device which may be used for performing various embodiments.

FIG. 14 is a system block diagram of a computing device 1400 useful for performing and implementing the various embodiments described above. The computing device 1300 may perform the functions of a control system 113, 213, 910, 1313 for an imaging system and/or a system for processing x-ray image data. While the computing device 1400 is illustrated as a laptop computer, a computing device providing the functional capabilities of the computer device 1400 may be implemented as a workstation computer, an embedded computer, a desktop computer, a server computer or a handheld computer (e.g., tablet, a smartphone, etc.). A typical computing device 1400 may include a processor 1401 coupled to an electronic display 1404, a speaker 1406 and a memory 1402, which may be a volatile memory as well as a nonvolatile memory (e.g., a disk drive). When implemented as a laptop computer or desktop computer, the computing device 1400 may also include a floppy disc drive, compact disc (CD) or DVD disc drive coupled to the processor 1401. The computing device 1400 may include an antenna 1410, a multimedia receiver 1412, a transceiver 1418 and/or communications circuitry coupled to the processor 1401 for sending and receiving electromagnetic radiation, connecting to a wireless data link, and receiving data. Additionally, the computing device 1400 may include network access ports 1424 coupled to the processor 1401 for establishing data connections with a network (e.g., LAN coupled to a service provider network, etc.). A laptop computer or desktop computer 1400 typically also includes a keyboard 1414 and a mouse pad 1416 for receiving user inputs.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored on as one or more instructions or code on a non-transitory computer-readable medium. The steps of a method or algorithm disclosed herein may be embodied in a processor-executable software module executed which may reside on a non-transitory computer-readable medium. Non-transitory computer-readable media includes computer storage media that facilitates transfer of a computer program from one place to another. A storage media may be any available media that may be accessed by a computer. By way of example, and not limitation, such non-transitory computer-readable storage media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of non-transitory computer-readable storage media. Additionally, the operations of a method or algorithm may reside as one or any combination or set of codes and/or instructions on a machine readable medium and/or computer-readable medium, which may be incorporated into a computer program product.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. An x-ray imaging system, comprising:
    an O-shaped gantry including a housing and defining an imaging bore;
    an x-ray source located within the housing of the gantry;
    a detector system located within the housing of the gantry opposite the x-ray source, the detector system including a plurality of x-ray sensitive detector elements defining a contiguous detector area having an elongated central portion and a pair of peripheral portions arranged on opposing sides of the central portion to define a panel region; and
    a drive system for rotating the x-ray source and the detector system around the imaging bore;
    wherein the central portion defines a central portion length and a central portion width, and the panel region defines a panel length and a panel width, the central portion length being greater than the panel length, and the panel width being greater than the central portion width.

2. The x-ray imaging system of claim 1, wherein the x-ray source includes an adjustable collimator configured to direct a beam of x-ray radiation onto the central portion of the detector area to perform a fan-beam computed tomography (CT) imaging scan.

3. The x-ray imaging system of claim 2, wherein the adjustable collimator is further configured to direct a beam of x-ray radiation onto to the panel region of the detector area to perform 2D x-ray fluoroscopy and/or cone-beam CT imaging.

4. The x-ray imaging system of claim 3, wherein the central portion of the detector area is configured to collect at least 32 slices of x-ray data simultaneously as the x-ray source and detector system rotate within the gantry during a fan-beam computed tomography (CT) imaging scan.

5. The x-ray imaging system of claim 1, wherein the detector elements include:
    a layer of scintillator material;
    a photodiode array optically coupled to the layer of scintillator material; and
    an electronics assembly coupled directly behind the photodiode array and including an analog-to-digital (A/D) converter for converting output signals from the photodiode array to digital signals.

6. The x-ray imaging system of claim 5, wherein the layer of scintillator material includes gadolinium oxysulfide (GOS).

7. The x-ray imaging system of claim 5, wherein the detector system is configured to read-out a plurality of frames of image data while the detector elements are continuously exposed to x-ray radiation from the x-ray source.

8. The x-ray imaging system of claim 1, wherein adjacent x-ray sensitive detector elements are spaced from each other at a common spacing distance.

9. The x-ray imaging system of claim 8, wherein a spacing ratio of the central portion length to the spacing distance is greater than 250:1.

10. The x-ray imaging system of claim 8, wherein the spacing distance is less than 2 millimeters.

11. The x-ray imaging system of claim 1, further comprising an anti-scatter apparatus located over the contiguous detector area.

12. The x-ray imaging system of claim 1, wherein the detector system defines a detector surface that is curved or angled along its length and defines a semicircular arc centered on a focal spot of the x-ray source.

13. The x-ray imaging system of claim 12, wherein the detector surface is further curved or angled along its width and defines a semicircular arc centered on the focal spot of the x-ray source.

14. The x-ray imaging system of claim 1, wherein the detector system includes a multiple buffering configuration configured such that at least one buffer reads-out previously-collected digital image data while new digital image data accumulates in another buffer.

15. The x-ray imaging system of claim 1, further comprising an apparatus for moving the detector elements relative to the x-ray source by a sub-pixel amount.

16. The x-ray imaging system of claim 15, further comprising a processing device coupled to the detector system and being configured with processor-executable instructions to perform operations including:
    receiving, from the detector system, a plurality of first x-ray images of an object with a first spatial resolution that are obtained while the detector elements are moved relative to the x-ray source; and
    generating at least one second image of the object using the plurality of first x-ray images, wherein the at least one second image is a super resolution (SR) image that has a greater spatial resolution and/or signal-to-noise (SNR) ratio compared to the first x-ray images.

17. The x-ray imaging system of claim 16, wherein a width ratio of the panel width to the central portion width is at least 1.2:1.

18. The x-ray imaging system of claim 1, wherein a length ratio of the central portion length to the panel length is at least 1.25:1.

19. The x-ray imaging system of claim 1, wherein a length ratio of the central portion length to the panel length is at least 2:1.

20. The x-ray imaging system of claim 19, wherein a width ratio of the panel width to the central portion width is at least 1.2:1.

21. The x-ray imaging system of claim 1, wherein the central portion length is at least 1 meter.

22. The x-ray imaging system of claim 21, wherein the central portion length is less than 0.5 meters; and
    wherein the central portion width is greater than 0.3 meters.

* * * * *